(12) United States Patent
Ashkenazi et al.

(10) Patent No.: US 12,296,094 B1
(45) Date of Patent: May 13, 2025

(54) DEVICES AND METHODS FOR TREATING LUNG DISEASES

(71) Applicants: Tel HaShomer Medical Research Infrastructure and Services Ltd., Ramat-Gan (IL); Ramot at Tel-Aviv University Ltd., Tel-Aviv (IL)

(72) Inventors: Moshe Ashkenazi, Ganei-Tikva (IL); Gil Sokol, Ganey-Tikva (IL); Ori Efrati, Herzliya (IL); Itzik Mashiach, Tel-Aviv (IL); Diana Sverdlov, Tel-Aviv (IL); Ortal Shtayman, Tel-Aviv (IL); Imry Ben Avi, Tel-Aviv (IL); Daniel Sorkin, Tel-Aviv (IL)

(73) Assignees: Tel HaShomer Medical Research Infrastructure and Services Ltd., Ramat-Gan (IL); Ramot at Tel-Aviv University Ltd., Tel-Aviv (IL)

( * ) Notice: Subject to any disclaimer, the term of this patent is extended or adjusted under 35 U.S.C. 154(b) by 893 days.

(21) Appl. No.: 17/239,880

(22) Filed: Apr. 26, 2021

Related U.S. Application Data

(60) Provisional application No. 63/015,581, filed on Apr. 26, 2020.

(51) Int. Cl.
*A61M 16/00* (2006.01)
*A61M 16/20* (2006.01)

(52) U.S. Cl.
CPC ........ *A61M 16/022* (2017.08); *A61M 16/202* (2014.02); *A61M 16/0009* (2014.02)

(58) Field of Classification Search
None
See application file for complete search history.

(56) References Cited

U.S. PATENT DOCUMENTS

| 3,964,482 A | 6/1976 | Gerstel et al. |
| 5,797,898 A | 8/1998 | Santini, Jr. et al. |

(Continued)

FOREIGN PATENT DOCUMENTS

| CA | 2406185 | 10/2001 |
| WO | WO 2006/078451 | 7/2006 |

(Continued)

OTHER PUBLICATIONS

Agusti et al. "What Does Endotyping Mean for Treatment in Chronic Obstructive Pulmonary Disease?", The Lancet, 390(10098): 980-987, Sep. 2, 2017.

(Continued)

*Primary Examiner* — Joseph D. Boecker
*Assistant Examiner* — Thomas W Greig

(57) ABSTRACT

Pulmonary treatment methods and systems. During pulmonary treatment breath cycles, a hold period of elevated inspiration pressure may promote lung region filling (and potentially recruitment) via collateral airways. Expectoration is promoted by dropping from the inspiration pressure to an undershoot pressure; de-recruitment (e.g., by airway collapse) is mitigated by raising the undershoot pressure to a positive expiratory pressure (PEP) during expiration phase. Breath cycles with a period of post-PEP suction may also be administered. Respiratory therapy systems may be programmed or re-programmed to administer this pressure protocol. In some embodiments, a system includes a hand-held unit including a patient mouthpiece, a base unit which provides pressurized gas to the mouthpiece, an electronically controllable valve in the hand-held unit for providing therapy maneuvers such as PEP (Positive Expiratory Pressure) through the mouthpiece, and a computing unit which instructs the hand-held unit to perform therapy maneuvers.

22 Claims, 19 Drawing Sheets

(56) References Cited

U.S. PATENT DOCUMENTS

| | | | |
|---|---|---|---|
| 5,934,272 | A | 8/1999 | Lloyd et al. |
| 6,158,432 | A * | 12/2000 | Biondi ................. A61M 16/026 |
| | | | 128/204.22 |
| 6,167,881 | B1 | 1/2001 | Hughes |
| 6,557,549 | B2 | 5/2003 | Schmidt et al. |
| 6,609,517 | B1 * | 8/2003 | Estes ................... A61M 16/204 |
| | | | 128/204.23 |
| 6,860,265 | B1 * | 3/2005 | Emerson ............. A61M 16/202 |
| | | | 128/205.12 |
| 7,824,366 | B2 | 11/2010 | Tanaka |
| 8,038,633 | B2 | 10/2011 | Van Brunt et al. |
| 8,523,782 | B2 | 9/2013 | Freitag et al. |
| 8,875,705 | B2 | 11/2014 | Avni |
| 9,114,219 | B2 | 8/2015 | Kimm et al. |
| 9,636,472 | B2 * | 5/2017 | Rueller ................. A61M 16/00 |
| 10,485,941 | B2 | 11/2019 | Brand |
| 10,518,048 | B2 * | 12/2019 | Bobey ................... A61H 31/00 |
| 2007/0267010 | A1 * | 11/2007 | Fink ...................... A61M 16/08 |
| | | | 128/200.23 |
| 2008/0156319 | A1 | 7/2008 | Avni |
| 2012/0247466 | A1 | 10/2012 | Avni |
| 2014/0190481 | A1 | 7/2014 | Jam |
| 2014/0257151 | A1 | 9/2014 | Chikkanaravangala et al. |
| 2015/0040891 | A1 | 2/2015 | Avni |
| 2018/0043116 | A1 * | 2/2018 | Birnkrant ............. A61H 9/0007 |
| 2018/0311461 | A1 * | 11/2018 | Millar ................. A61M 16/209 |
| 2020/0206454 | A1 * | 7/2020 | Lurie ................. A61M 16/0825 |
| 2021/0128851 | A1 * | 5/2021 | Nitta ................. A61M 16/0066 |

FOREIGN PATENT DOCUMENTS

| | | |
|---|---|---|
| WO | WO 2007106804 | 9/2007 |
| WO | WO 2010/038233 | 4/2010 |
| WO | WO 2015/198001 | 12/2015 |

OTHER PUBLICATIONS

Alves et al. "Performance Analysis of the Flutter VRP1 Under Different Flows and Angles", Respiratory Care, 53(3): 316-323, Mar. 2008.

Bonini et al. "The Role of the Small Airways in the Pathophysiology of Asthma and Chronic Obstructive Pulmonary Disease", Therapeutic Advances in Respiratory Disease, 9(6): 281-293, Published Online Jun. 2, 2015.

Cantin et al. "Mechanical Airway Clearance Using the Frequencer Electro-Acoustical Transducer in Cystic Fibrosis", Clinical and Investigative Medicine, 29(3): 159-165, Jun. 2006.

Chatburn "High-Frequency Assisted Airway Clearance", Respiratory Care, 52(9): 1224-1235, Sep. 2007.

Henke et al. "Effects of High-Frequency Oscillating Pressures on Upper Airway Muscles in Humans", Journal of Applied Physiology, 75(2): 856-862, Aug. 1993.

Kempainen et al. "Comparison of High-Frequency Chest Wall Oscillation With Differing Waveforms for Airway Clearance in Cystic Fibrosis", Chest, 132(4): 1227-1232, Published Online Sep. 21, 2007.

Konstan et al. "Efficacy of the Flutter Device for Airway Mucus Clearance in Patients With Cystic Fibrosis", The Journal of Pediatrics, 124(5/Pt.1): 689-693, May 1994.

Myers "Year in Review 2014: Aerosol Delivery Devices", Respiratory Care, 60(8): 1190-1196, Aug. 2015.

Rabe et al. "Chronic Obstructive Pulmonary Disease", The Lancet, 389(10082): 1931-1940, May 13, 2017.

Sokol et al. "The Sort-Term Effect of Breathing Tasks via an Incentive Spirometer on Lung Function Compared With Autogenic Drainage in Subjects With Cystic Fibrosis", Respiratory Care, 60(12): 1819-1825, Dec. 2015.

Terry et al. "The Clinical Significance of Collateral Ventilation", Annals of the American Thoracic Society, 13(12): 2251-2257, Dec. 2016.

Volsko et al. "Performance Comparison of Two Oscillating Positive Expiratory Pressure Devices: Acapella Versus Flutter", Respiratory Care, 48(2): 124-130, Feb. 2003.

\* cited by examiner

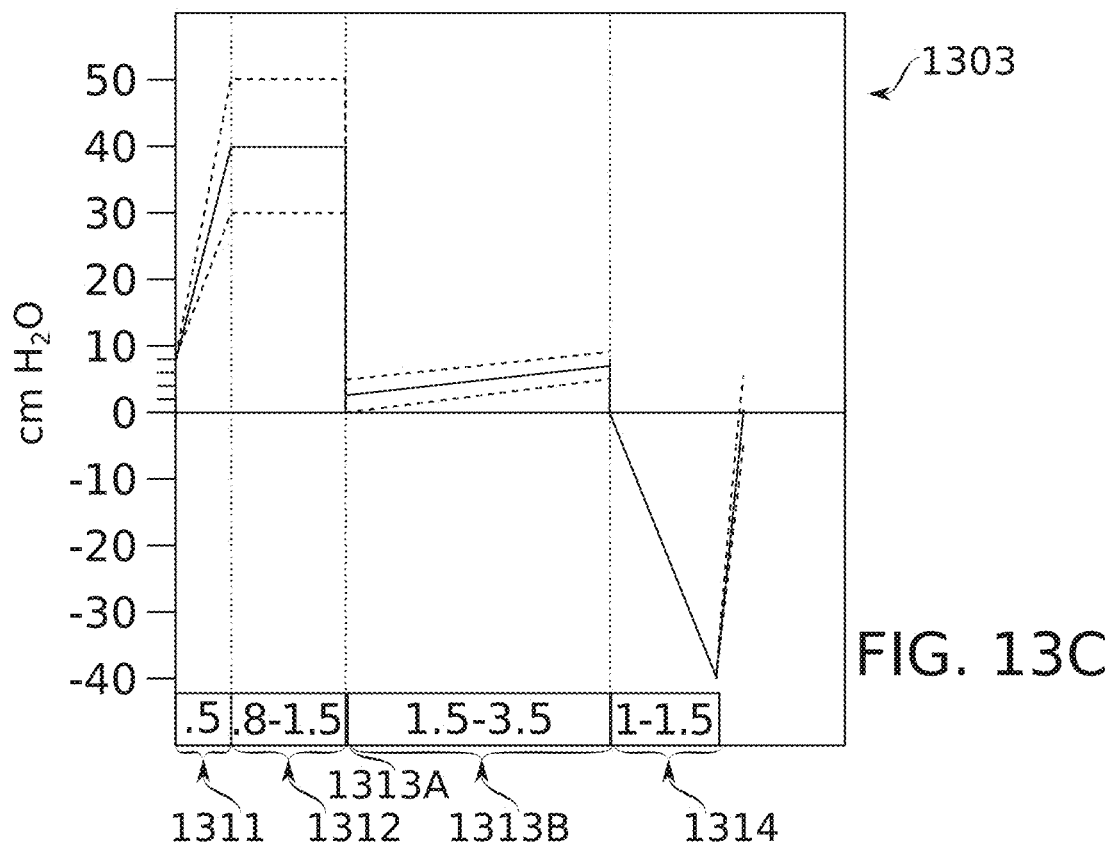
FIG. 13C
FIG. 14
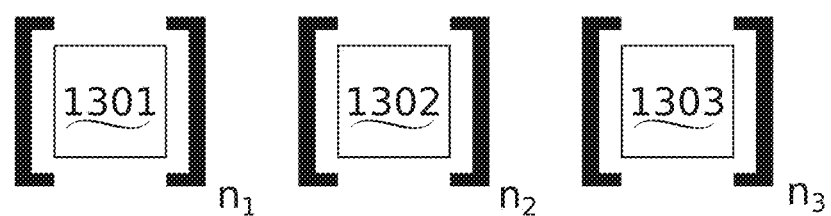

DEVICES AND METHODS FOR TREATING LUNG DISEASES

RELATED APPLICATION(S)

This application claims the benefit of priority under 35 USC 119(e) of U.S. Provisional Patent Application No. 63/015,581 filed on Apr. 26, 2020, the contents of which are all incorporated by reference as if fully set forth herein in their entirety.

FIELD AND BACKGROUND OF THE INVENTION

The present invention, in some embodiments thereof, relates to a device and methods for treating lung disease; such as, for example, asthma, chronic obstructive pulmonary disease (COPD), pneumonia, acute respiratory distress syndrome, virally-induced lung disease, and/or other obstructive lung diseases treated with the use of a respiratory ventilator.

Obstructive lung diseases such as these are characterized by persistent airflow limitation caused by small airways disease and/or alveolar septum destruction and/or impaired secretions clearance. Chronic inflammation causes structural changes and narrowing of the small airways. Destruction of the lung parenchyma, also by inflammatory process, leads to loss of alveolar attachments to the walls of the small airways and reduces an outward pulling and tethering of the walls of the small airways, which normally keeps them open. These changes diminish an ability of the airways to remain open, particularly during expiration with some of these airways, particularly in dependent regions of the lung, becoming shut close throughout the respiratory cycle and opening up with deep inhalation (a sigh). Hyper secretion of mucus due to increased number of goblet cells and enlarged sub mucosal glands contribute to the tendency of the small airways to close up during part or all of the respiratory cycle, resulting in reduced alveolar ventilation of these lung regions. The disease process includes remodeling of the small-airway compartment and loss of elastic recoil by emphysematous destruction of parenchyma resulting in a progressive decline of Forced Expiratory Volume as measured in 1 second (FEV1), inadequate lung emptying on expiration, and subsequent migration of locations of static and dynamic hyper-inflation.

In addition to obstructive lung disease such as asthma and COPD, there are additional chronic supportive lung diseases that have different etiologies but share similar pathophysiological changes. These diseases include cystic fibrosis (CF), one of the most prevalent lethal genetic disease in the western world. More prevalent than CF is a new group of pathologies referred to as non-CF bronchiectasis. Other diseases that have similar pulmonary manifestations are immune deficiencies (primary or secondary), Primary Ciliary Dyskinesia and more.

Additional background art includes:

Rabe K F, Watz H. "Chronic obstructive pulmonary disease." Lancet. 2017 May 13; 389(10082):1931-1940;

Agustí A, Celli B, Faner R. "What does endotyping mean for treatment in chronic obstructive pulmonary disease?" Lancet. 2017 Sep. 2; 390(10098):980-987;

An article titled "Efficacy of the FLUTTER@device for airway mucus clearance in patients with cystic fibrosis" by Konstan M W, Stern R C, Doershuk C F, published in J Pediatrics May 1994; 124:689-693;

An article titled "Performance Analysis of the Flutter VRP1 under Different Flows and Angles" by Luiz Antonio Alves P T MSc, Fá bio Pitta P T PhD, and Antonio Fernando Brunetto P T PhD, published in Respir Care 2008; 53(3):316-323;

An article titled "Performance Comparison of Two Oscillating Positive Expiratory Pressure Devices Acapella Versus Flutter", by Teresa A Volsko RRT FAARC, Juliann M DiFiore, and Robert L Chatburn RRT FAARC, published in Respir Care 2003; 48(2):124-130;

An article titled "Mechanical airway clearance using the Frequencer electro-acoustical transducer in cystic fibrosis" by André M. Cantin, Marc Bacon, Yves Berthiaume, published in Clin Invest Med 2006; 29 (3): 159-165;

An article titled "Comparison of High-Frequency Chest Wall Oscillation with Differing Waveforms for Airway Clearance in Cystic Fibrosis" by Robert R. Kempainen, MD; Cynthia B. Williams, CRTT, RCP; Ann Hazelwood, CRTT, RCP; Bruce K. Rubin, MD, published in MEngr, FCCP and Carlos E. Milla, MD;

An article titled "High-frequency assisted airway clearance" by Chatburn R L, published in Respir Care. 2007 September; 52(9):1224-35;

An article titled "Effects of high-frequency oscillating pressures on upper airway muscles in humans" by Henke K G, Sullivan C E, published in J Appl Physiol. 1993 August; 75(2):856-62;

An article titled "The Short-Term Effect of Breathing Tasks Via an Incentive Spirometer on Lung Function Compared With Autogenic Drainage in Subjects With Cystic Fibrosis" by Sokol G, et al., published in Respir Care. 2015 December; 60(12):1819-25;

International Patent Application Publication No. WO 2015/198001;

International Patent Application Publication No. WO 2010/038233;

International Patent Application Publication No. WO 2006/078451;

U.S. Patent Application Publication No. 2015/0040891;
U.S. Patent Application Publication No. 2014/0257151;
U.S. Patent Application Publication No. 2014/0190481;
U.S. Patent Application Publication No. 2012/0247466;
U.S. Patent Application Publication No. 2008/0156319;
CA Patent Application No. 2406185;
EP Patent Application No. 2007461
U.S. Pat. No. 8,875,705;
U.S. Pat. No. 8,523,782;
U.S. Pat. No. 8,038,633;
U.S. Pat. No. 7,824,366;
U.S. Pat. No. 6,167,881;
U.S. Pat. No. 6,557,549;
U.S. Pat. No. 5,797,898;
U.S. Pat. No. 5,934,272; and
U.S. Pat. No. 3,964,482.

The disclosures of all references mentioned above and throughout the present specification, as well as the disclosures of all references mentioned in those references, are hereby incorporated herein by reference.

SUMMARY OF THE INVENTION

According to an aspect of some embodiments of the present disclosure, there is provided a respiratory therapy device configured to establish pressures within a patient's lung to establish mechanical control of breathing, and including a controller configured to command pressure delivery to lungs in a sequence that implements, during each of one or more breath cycles: a period of positive inspiration pressure extended to pressurize de-recruited lung regions via collateral airways; reduction from the positive pressure down to an undershoot pressure, allowing pressure in the pressurized de-recruited lung regions to mobilize mucous along main branch airways of the lung; and elevation of pressure from the undershoot pressure to a positive expiratory pressure, before the lung volume reaches a breath cycle minimum.

According to some embodiments of the present disclosure, the positive inspiration pressure is within a range of about 30-50 cm $H_2O$.

According to some embodiments of the present disclosure, the period of positive inspiration pressure is extended to a period between about 0.8 seconds and 5 seconds, after an inspirium rump period.

According to some embodiments of the present disclosure, the undershoot pressure is below 5 cm $H_2O$.

According to some embodiments of the present disclosure, the undershoot pressure is at or above 0 cm $H_2O$.

According to some embodiments of the present disclosure, the elevation of pressure is to a positive expiratory pressure between about 5 cm $H_2O$ and 9 cm $H_2O$.

According to some embodiments of the present disclosure, the elevation of pressure to the positive expiratory pressure occurs over a period of about 1.5-3.5 seconds.

According to some embodiments of the present disclosure, within at least one of the one or more breath cycles: after pressure increases to the positive expiratory pressure, a suction period is administered.

According to some embodiments of the present disclosure, suction pressure during the suction period reaches a lower pressure value within a range between about −20 cm $H_2O$ and about −40 cm $H_2O$.

According to an aspect of some embodiments of the present disclosure, there is provided a method of manufacturing a medical device, including programming, re-programming, or replacing a controller of a respiratory device; wherein the programmed, re-programmed, or replacement controller is configured to command pressure delivery to lungs in a sequence that implements, during each of one or more breath cycles: a period of positive inspiration pressure extended to pressurize de-recruited lung regions via collateral airways, reduction from the positive pressure down to an undershoot pressure, allowing pressure in the pressurized de-recruited lung regions to mobilize mucous along main branch airways of the lung, and elevation of pressure from the undershoot pressure to a positive expiratory pressure, before the lung volume reaches a breath cycle minimum.

According to an aspect of some embodiments of the present disclosure, there is provided a method of using pressure to recruit lung regions of a patient, the method including administering, during each of one or more breath cycles: a period of positive inspiration pressure extended to pressurize de-recruited lung regions via collateral airways; reduction from the positive pressure down to an undershoot pressure, allowing pressure in the pressurized de-recruited lung regions to mobilize mucous along main branch airways of the lung; and elevation of pressure from the undershoot pressure to a positive expiratory pressure, before the lung volume reaches a breath cycle minimum.

According to some embodiments of the present disclosure, the positive inspiration pressure is within a range of about 30-50 cm $H_2O$.

According to some embodiments of the present disclosure, the period of positive inspiration pressure is extended to a period between about 0.8 seconds and 5 seconds, after an inspirium rump period.

According to some embodiments of the present disclosure, the undershoot pressure is below 5 cm $H_2O$.

According to some embodiments of the present disclosure, the undershoot pressure is at or above 0 cm $H_2O$.

According to some embodiments of the present disclosure, the elevation of pressure is to a positive expiratory pressure between about 5 cm $H_2O$ and 9 cm $H_2O$.

According to some embodiments of the present disclosure, the elevation of pressure to the positive expiratory pressure occurs over a period of about 1.5-3.5 seconds.

According to some embodiments of the present disclosure, within at least one of the one or more breath cycles: after pressure increases to the positive expiratory pressure, a suction period is administered.

According to some embodiments of the present disclosure, suction pressure during the suction period reaches a lower pressure value within a range between about −20 cm $H_2O$ and about −40 cm $H_2O$.

According to some embodiments of the present disclosure, the administering is performed as a treatment for viral pneumonia.

According to some embodiments of the present disclosure, the viral pneumonia is caused by a coronavirus.

According to some embodiments of the present disclosure, the coronavirus is SARS-COV-2, and the viral pneumonia is a symptom of COVID-19.

According to an aspect of some embodiments of the present disclosure, there is provided a method of using pressure from a ventilator to recruit lung regions of a patient, the method including administering, over one or more breath cycles, a protocol including an inhalation phase and an exhalation phase; and wherein: during the inhalation phase, the ventilator maintains positive inspiration pressure within a range of about 30-50 cm $H_2O$ of pressure for a high positive pressure period between about 0.8 seconds and 5 seconds, after an inspirium rump period; at onset of the exhalation phase, the ventilator decreases pressure to a minimum pressure below 5 cm $H_2O$; and after the decrease in pressure and during the exhalation phase, the ventilator increases pressure to a positive expiratory pressure within a range between about 5 cm $H_2O$ and 9 cm $H_2O$, before the lungs of the patient reach their minimum volume during the exhalation phase.

According to some embodiments of the present disclosure, the minimum pressure is above about −5 cm $H_2O$.

According to some embodiments of the present disclosure, the minimum pressure is at or above about 0 cm $H_2O$.

According to some embodiments of the present disclosure, after the decrease in pressure and during the exhalation phase, the ventilator increases pressure through a range of pressures including a lower pressure, an upper pressure, and the positive expiratory pressure.

According to some embodiments of the present disclosure, the lower pressure is the minimum pressure.

According to some embodiments of the present disclosure, the upper pressure is in a range between about 3 cm $H_2O$ and 10 cm $H_2O$.

According to some embodiments of the present disclosure, the upper pressure is also the positive expiratory pressure.

According to some embodiments of the present disclosure, the protocol re-recruits lung tissue by inflation via collateral airways during the inhalation phase, and maintains recruitment by preventing collapse using positive pressure during the expiration phase.

According to some embodiments of the present disclosure, the high positive pressure period is within a range of about 1 second to about 1.5 seconds.

According to some embodiments of the present disclosure, after the ventilator increases pressure to the positive expiratory pressure, the ventilation decreases pressure, during a suction period, to a suction pressure within a range between about −20 cm $H_2O$ and about −40 cm $H_2O$.

According to some embodiments of the present disclosure, the high positive pressure period is selected to target recruitment in relatively larger airways, compared to airways at an alveolar level.

According to some embodiments of the present disclosure, the duration of the high positive pressure period is between about 1.5 and 3.5 seconds.

According to some embodiments of the present disclosure, the high positive pressure period is selected to target recruitment in relatively smaller airways including airways at an alveolar level.

According to some embodiments of the present disclosure, a duration of the high positive pressure period is between about 0.8 and 1.5 seconds.

According to some embodiments of the present disclosure, the protocol aspirates mucous by suction, after recruitment of lung tissue by inflation via collateral airways during the inhalation phase.

According to some embodiments of the present disclosure, tissue recruited by inflation via collateral airways during the inhalation phase maintains recruitment at least in part by preventing collapse using positive pressure during the expiration phase.

According to some embodiments of the present disclosure, tissue inflated via collateral airways during the inhalation phase resists collapse during the suction period at least in part due to proximal movement of mucous plugs.

According to some embodiments of the present disclosure, the protocol is administered in each of a plurality of breath cycles within a sequence of breaths, and wherein: within a first one or more administrations during the plurality of breath cycles, the positive expiratory pressure is followed by initiation of the next inspiratory phase without suction; and within a second one or more administrations during the plurality of breath cycles following the first one or more administrations, the positive expiratory pressure is followed by a period of suction before the next inspiratory phase.

According to some embodiments of the present disclosure, during the second one or more administrations, the duration of the high positive pressure period is between about 1.5 and 3.5 seconds in at least one of the administrations, and between about 0.8 and 1.5 seconds in another at least one of the administrations.

According to some embodiments of the present disclosure, the administrations with different high positive pressure periods differentially target collateral inflation in lung regions at different positions along a proximal-to-distal direction within the lung.

According to some embodiments of the present disclosure, the method includes monitoring pulmonary pressure using a sensor, and beginning administration of the protocol, based on a spontaneous change in sensed pulmonary pressure.

According to some embodiments of the present disclosure, the change in sensed pulmonary pressure is due to a cough initiated by the patient.

According to some embodiments of the present disclosure, the change in the sensed pulmonary pressure includes a change to a more negative pressure.

According to some embodiments of the present disclosure, the method includes monitoring pulmonary pressure using a sensor during administration of the protocol, and interrupting administration of the protocol, based on a spontaneous change in the sensed pulmonary pressure.

According to some embodiments of the present disclosure, the change in sensed pulmonary pressure is due to a cough initiated by the patient.

According to some embodiments of the present disclosure, the change in the sensed pulmonary pressure includes a change to a more negative pressure.

According to some embodiments of the present disclosure, the method includes resuming administration of the protocol, after the spontaneous change in the sensed pulmonary pressure.

According to some embodiments of the present disclosure, the protocol is administered as a treatment for viral pneumonia.

According to some embodiments of the present disclosure, the viral pneumonia is caused by a coronavirus.

According to some embodiments of the present disclosure, the coronavirus is SARS-COV-2, and the viral pneumonia is a symptom of COVID-19.

According to an aspect of some embodiments of the present disclosure, there is provided a method of using pressure from a ventilator to re-recruit de-recruited lung regions of a patient, the method including administering, over one or more breath cycles, a protocol including an inhalation phase and an exhalation phase; and wherein: during the inhalation phase, the ventilator maintains pressure within a range of about 30-50 cm $H_2O$ of pressure for a high positive pressure period between about 0.8 seconds and 5 seconds, after an inspirium rump period; at onset of the exhalation phase, the ventilator decreases pressure to a first range of exhalation pressures for a period including at least 1.5 seconds at a positive expiratory pressure; and then, during a suction period, the ventilator decreases pressure to a suction pressure within a range between about −20 cm $H_2O$ and about −40 cm $H_2O$.

According to an aspect of some embodiments of the present disclosure, there is provided a method of using pressure from a ventilator to re-recruit de-recruited lung regions of a patient, the method including administering, over one or more breath cycles, a protocol including an inhalation phase and an exhalation phase; and wherein: during the inhalation phase, the ventilator maintains pressure within a range of about 8-40 cm $H_2O$ of pressure for a hold period between about 1-3 seconds; and at onset of the exhalation phase, the ventilator decreases pressure to a positive expiratory pressure lower than the inhalation phase pressure, and within a range between about 2 cm $H_2O$ and 8 cm $H_2O$.

According to some embodiments of the present disclosure, the positive expiratory pressure is maintained for 2-3.5 seconds after the onset of the exhalation phase until the next inhalation phase begins.

According to some embodiments of the present disclosure, the positive expiratory pressure is maintained for 0.5-2.5 seconds, and is followed by suction to a pressure within a range of −20 to −40 cm $H_2O$ before the next inhalation phase begins.

According to some embodiments of the present disclosure, the suction pressure is held for between 0.5 and 2.5 seconds.

According to some embodiments of the present disclosure, the protocol is administered in each of a plurality of breath cycles within a sequence of breaths, and wherein: within a first one or more administrations during the plurality of breath cycles, the positive expiratory pressure is maintained for 2-3.5 seconds after the onset of the exhalation phase until the next inhalation phase begins; and within a second one or more administrations during the plurality of breath cycles following the first one or more administrations, the positive expiratory pressure is maintained for 0.5-2.5 seconds after the onset of the exhalation phase, and is followed by suction to a pressure within a range of −20 to −40 cm $H_2O$ before the next inhalation phase begins.

According to some embodiments of the present disclosure, during the sequence of breaths, and following the plurality of breath cycles having administrations, there is administered over one or more breath cycles of a medication mode of pulmonary therapy applying medicine to the lungs, and including an inhalation phase and an exhalation phase; and wherein, during the inhalation phase of the medication mode of pulmonary therapy, the ventilator maintains pressure within a range of about 8-40 cm $H_2O$ of pressure for a period between about 1-3 seconds, during which the inhalation phase period the medicine is released to the lungs.

According to some embodiments of the present disclosure, at onset of the exhalation phase of the medication mode of pulmonary therapy, the ventilator decreases pressure to a positive expiratory pressure lower than the inhalation phase pressure, and within a range between about 1 cm $H_2O$ and 8 cm $H_2O$.

According to some embodiments of the present disclosure, the sequence of breaths includes one or more idle time breaths during which no hold period during inhalation is performed.

An aspect of some embodiments relates to providing pulmonary treatment for opening up small airways and providing pulmonary medicine by inhalation when the small airways are more open than prior to the pulmonary treatment.

According to an aspect of some embodiments of the present invention there is provided a system for providing pulmonary treatment, the system including a hand-held unit including a mouthpiece for placing in or over a patient's mouth, an air tube for leading a flow of gas to or from the patient's mouth, a base unit for providing the flow of air as air under pressure or as suction, an electronically controllable valve in the hand-held unit, configured to be controllable for providing PEP (Positive Expiratory Pressure) maneuvers to the patient via the mouthpiece, and a computing unit arranged to control the hand-held unit to perform the PEP maneuvers.

According to some embodiments of the invention, the system further includes a pulmonary sensor, the pulmonary sensor configured to send pulmonary measurement data to the computing unit, and wherein the computing unit is configured to receive the data measured by the pulmonary sensor and analyze the data, producing an analysis, and to activate the valve based on the analysis.

According to some embodiments of the invention, the system further includes a metered dose provider.

According to some embodiments of the invention, the computing unit is configured to control the time that the metered dose provider provides medicine, based on the analysis.

According to some embodiments of the invention, the computing unit is configured to control what does of medicine the metered dose provider provides, based on the analysis.

According to an aspect of some embodiments of the present invention there is provided a method for providing pulmonary treatment, the method including providing pulmonary physical therapy to a patient including performing PEP (Positive Expiratory Pressure) maneuvers on the patient, sensing a patient's pulmonary status by a same device which provides the pulmonary physical therapy, and determining when to administer inhalatory pulmonary medicine to the patient based on the sensing.

According to some embodiments of the invention, the pulmonary physical therapy includes both PEP and suction.

According to an aspect of some embodiments of the present invention there is provided a system for collecting pulmonary data from patients and providing pulmonary physical treatment, the system including a pulmonary sensor, a computing unit arranged to receive data measured by the pulmonary sensor and analyze the data, producing an analysis, and a pulmonary physical treatment unit configured for providing pulmonary physical treatment when controlled by the computing unit, wherein the computing unit is arranged to determine whether to control the pulmonary physical treatment unit to provide pulmonary physical treatment based on the data.

According to some embodiments of the invention, the computing unit is configured to determine a duration of providing pulmonary physical treatment.

According to some embodiments of the invention, the computing unit is configured to sense when a subject is exhaling, and to control the pulmonary physical treatment unit to provide pulmonary physical treatment during exhalation.

According to some embodiments of the invention, the computing unit is configured to sense when a subject is exhaling, and to control the pulmonary physical treatment unit to provide pulmonary physical treatment when the subject is not exhaling.

According to some embodiments of the invention, the pulmonary physical treatment includes suction.

According to some embodiments of the invention, the computing unit is configured to sense when a subject is inhaling, and to control the pulmonary physical treatment unit to provide pulmonary physical treatment during inhalation.

According to some embodiments of the invention, the computing unit is configured to sense when a subject is inhaling, and to control the pulmonary physical treatment unit to provide pulmonary physical treatment when the subject is not inhaling.

According to some embodiments of the invention, the pulmonary physical treatment includes providing air under positive pressure.

According to some embodiments of the invention, the computing unit is configured to determine whether to provide medicine based on the data.

According to some embodiments of the invention, the computing unit is configured to determine how much medicine to provide based, at least in part, on the data.

According to some embodiments of the invention, the computing unit is configured to determine when to provide medicine based, at least in part, on the data.

According to an aspect of some embodiments of the present invention there is provided a method for providing pulmonary physical treatment, the method including measuring pulmonary data, using a computing unit for analyzing the pulmonary data, determining whether to provide pulmonary physical treatment based on the analyzing, and providing pulmonary physical treatment based on the determining.

According to some embodiments of the invention, the determining whether to provide pulmonary physical treatment includes determining a duration of providing pulmonary physical treatment.

According to some embodiments of the invention, the method further includes using the computing unit to sense when a subject is exhaling, and providing pulmonary physical treatment during exhalation.

According to some embodiments of the invention, the method further includes using the computing unit to sense when a subject is exhaling, and providing pulmonary physical treatment when the subject is not exhaling.

According to some embodiments of the invention, the pulmonary physical treatment includes suction.

According to some embodiments of the invention, the method further includes using the computing unit to sense when a subject is inhaling, and providing pulmonary physical treatment during inhalation.

According to some embodiments of the invention, the method further includes using the computing unit to sense when a subject is inhaling, and providing pulmonary physical treatment when the subject is not inhaling.

According to some embodiments of the invention, the pulmonary physical treatment includes providing air under positive pressure.

According to some embodiments of the invention, the method further includes using the computing unit to determine whether to provide medicine based on the pulmonary data.

According to some embodiments of the invention, the method further includes using the computing unit to determine how much medicine to provide based, at least in part, on the data.

According to some embodiments of the invention, the method further includes using the computing unit to determine when to provide medicine based, at least in part, on the data.

According to some embodiments of the invention, the computing unit is configured to determine when to provide medicine before the providing of the pulmonary physical treatment.

According to some embodiments of the invention, the computing unit is configured to determine when to provide medicine during the providing of the pulmonary physical treatment.

According to some embodiments of the invention, the computing unit is configured to determine when to provide medicine after the providing of the pulmonary physical treatment.

According to an aspect of some embodiments of the present invention there is provided a system for collecting pulmonary data from patients and providing pulmonary medicine, the system including a pulmonary sensor, a computing unit arranged to receive data measured by the pulmonary sensor and analyze the data, producing an analysis, and a pulmonary medicine unit configured for dispensing pulmonary medicine when controlled by the computing unit, wherein the computing unit is arranged to determine whether to control the pulmonary medicine unit to provide pulmonary medicine based on the analysis.

According to some embodiments of the invention, the computing unit is configured to determine a duration of providing pulmonary medicine.

According to some embodiments of the invention, the computing unit is configured to sense when a subject is inhaling, and to control the pulmonary medicine unit to provide pulmonary medicine during inhalation.

According to some embodiments of the invention, the computing unit is configured to sense when a subject is exhaling, and to control the pulmonary medicine unit to provide pulmonary medicine when the subject is not exhaling.

According to some embodiments of the invention, the computing unit is configured to sense when a subject is inhaling, and to control the pulmonary medicine unit to provide pulmonary medicine when the subject is not inhaling.

According to some embodiments of the invention, the computing unit is configured to determine how much medicine to provide based, at least in part, on the pulmonary data.

According to some embodiments of the invention, the computing unit is configured to determine when to provide medicine based, at least in part, on the pulmonary data.

According to some embodiments of the invention, the computing unit is configured to determine a duration of providing pulmonary physical treatment.

According to some embodiments of the invention, the computing unit is configured to sense when a subject is exhaling, and to control the pulmonary physical treatment unit to provide pulmonary physical treatment during exhalation.

According to some embodiments of the invention, the computing unit is configured to sense when a subject is exhaling, and to control the pulmonary physical treatment unit to provide pulmonary physical treatment when the subject is not exhaling.

According to some embodiments of the invention, the pulmonary physical treatment includes suction.

According to some embodiments of the invention, the computing unit is configured to sense when a subject is inhaling, and to control the pulmonary physical treatment unit to provide pulmonary physical treatment during inhalation.

According to some embodiments of the invention, the computing unit is configured to sense when a subject is inhaling, and to control the pulmonary physical treatment unit to provide pulmonary physical treatment when the subject is not inhaling.

According to some embodiments of the invention, the pulmonary physical treatment includes providing air under positive pressure.

According to an aspect of some embodiments of the present invention there is provided a method for providing pulmonary medicine, the method including measuring pulmonary data, using a computer to analyze the pulmonary data, determining whether to provide pulmonary medicine based on the analyzing, and providing pulmonary medicine based on the determining.

According to some embodiments of the invention, the method further includes using the computer to determine a duration of providing pulmonary medicine.

According to some embodiments of the invention, the method further includes using the computer to sense when a subject is exhaling, and providing pulmonary medicine when the subject is not exhaling.

According to some embodiments of the invention, the method further includes using the computer to sense when a subject is inhaling, and providing pulmonary medicine during inhalation.

According to some embodiments of the invention, the method further includes using the computer to sense when a subject is inhaling, and providing pulmonary medicine when the subject is not inhaling.

According to some embodiments of the invention, the method further includes using the computer to determine how much medicine to provide based, at least in part, on the pulmonary data.

According to some embodiments of the invention, the method further includes using the computer to determine when to provide medicine based, at least in part, on the pulmonary data.

According to some embodiments of the invention, the method further includes using the computer to determine a duration of providing pulmonary physical treatment.

According to some embodiments of the invention, the method further includes using the computer to sense when a subject is exhaling, and providing pulmonary physical treatment during exhalation.

According to some embodiments of the invention, the method further includes using the computing unit to sense when a subject is exhaling, and providing pulmonary physical treatment when the subject is not exhaling.

According to some embodiments of the invention, the pulmonary physical treatment includes suction.

According to some embodiments of the invention, the method further includes using the computing unit to sense when a subject is inhaling, and providing pulmonary physical treatment during inhalation.

According to some embodiments of the invention, the method further includes using the computing unit to sense when a subject is inhaling, and providing pulmonary physical treatment when the subject is not inhaling.

According to some embodiments of the invention, the pulmonary physical treatment includes providing air under positive pressure.

According to some embodiments of the invention, the method further includes using the computing unit to determine when to provide medicine based, at least in part, on the data.

According to some embodiments of the invention, the computing unit is configured to determine when to provide medicine before the providing of the pulmonary physical treatment.

According to some embodiments of the invention, the computing unit is configured to determine when to provide medicine during the providing of the pulmonary physical treatment.

According to some embodiments of the invention, the computing unit is configured to determine when to provide medicine after the providing of the pulmonary physical treatment.

According to an aspect of some embodiments of the present disclosure there is provided a method of using pressure to recruit lung regions of a patient, the method including administering, during each of one or more breath cycles during an inspiratory phase, providing a period of positive inspiration pressure extended to pressurize de-recruited lung regions via collateral airways, during an expiratory phase, providing a reduction from the positive inspiration pressure down to an undershoot pressure, allowing pressure in pressurized de-recruited lung regions to mobilize mucous along main branch airways of the lung, and providing an elevation of pressure from the undershoot pressure to a positive expiratory pressure, before lung volume reaches a breath cycle minimum.

According to some embodiments of the disclosure, after a decrease in pressure and during the expiratory phase, gradually increasing positive expiratory pressure through a range of pressures including a lower pressure, an upper pressure and the positive expiratory pressure.

According to some embodiments of the disclosure, including, after the reduction from the positive inspiration pressure and during the expiratory phase, before lungs of the patient reach a minimum volume during the expiratory phase, increasing pressure to a positive expiratory pressure within a range between about 5 cm $H_2O$ and 9 cm $H_2O$.

According to some embodiments of the disclosure, providing pressure is performed by a device selected from a group consisting of a respiratory ventilator, a cough simulation device, a cough assistance system, and a mechanical insufflation-exsufflation device.

According to some embodiments of the disclosure, during the inspiratory phase, positive inspiration pressure is maintained within a range of about 30-50 cm $H_2O$ of pressure for a high positive pressure period between about 0.8 seconds and 5 seconds, after an inspirium rump period.

According to some embodiments of the disclosure, during the inspiratory phase, maintaining pressure within a range of about 8-40 cm $H_2O$ of pressure for a hold period between about 1-3 seconds.

According to some embodiments of the disclosure, at onset of the expiratory phase including decreasing pressure to a minimum pressure below 5 cm $H_2O$.

According to some embodiments of the disclosure, including decreasing pressure to a first range of expiratory pressures for a period including at least 1.5 seconds at a positive expiratory pressure at onset of the expiratory phase, and followed by, during a suction period, decreasing pressure to a suction pressure within a range between about −20 cm $H_2O$ and about −40 cm $H_2O$.

According to some embodiments of the disclosure, the positive expiratory pressure is maintained for 2-3.5 seconds after the onset of the expiratory phase until the next inspiratory phase begins.

According to some embodiments of the disclosure, the undershoot pressure is at or above about 0 cm $H_2O$.

According to some embodiments of the disclosure, the positive expiratory pressure is maintained for 0.5-2.5 seconds, and is followed by suction to a pressure within a range of −20 to −40 cm $H_2O$ before the next inspiratory phase begins.

According to some embodiments of the disclosure, within a first one or more administrations during a plurality of breath cycles, the positive expiratory pressure is followed by initiation of a next inspiratory phase without suction, and within a second one or more administrations during the plurality of breath cycles following the first one or more administrations, the positive expiratory pressure is followed by a period of suction before the next inspiratory phase.

According to some embodiments of the disclosure, within a first one or more administrations during a plurality of breath cycles, the positive expiratory pressure is maintained for 2-3.5 seconds after the onset of the expiratory phase until the next inspiratory phase begins, and within a second one or more administrations during the plurality of breath cycles following the first one or more administrations, the positive expiratory pressure is maintained for 0.5-2.5 seconds after the onset of the expiratory phase, and is followed by suction to a pressure within a range of −20 to −40 cm $H_2O$ before the next inspiratory phase begins.

According to some embodiments of the disclosure, including beginning or interrupting the administering based on monitoring pulmonary pressure using a sensor, and based on detecting a spontaneous change in sensed pulmonary pressure.

According to some embodiments of the disclosure, including, during a sequence of breaths, and following a plurality of breath cycles including administrations, there is administered over one or more breath cycles a medication mode of pulmonary therapy applying medicine to the lungs, including an inhalation phase and an expiratory phase, and wherein, during the inhalation phase of the medication mode of pulmonary therapy, maintaining pressure within a range of about 8-40 cm $H_2O$ of pressure for a period between about 1-3 seconds, during which the inspiratory phase medicine is released to the lungs.

According to some embodiments of the disclosure, at onset of an expiratory phase of the medication mode of pulmonary therapy, decreasing pressure to a positive expiratory pressure lower than pressure at the inhalation phase, and within a range between about 1 cm $H_2O$ and 8 cm $H_2O$.

According to some embodiments of the disclosure, the medicine is released to the lungs 1-3 second after initiation of the inhalation phase.

According to an aspect of some embodiments of the present disclosure there is provided a system for collecting pulmonary data from patients and providing pulmonary physical treatment, the system including a pulmonary sensor, a computing unit arranged to receive data measured by the pulmonary sensor and analyze the data, producing an analysis, and a pulmonary physical treatment unit for providing pulmonary physical treatment under control by the computing unit, wherein the computing unit is arranged to control the pulmonary physical treatment unit to provide pulmonary physical treatment based on the data, administering, during each of one or more breath cycles, treatment as follows during an inspiratory phase, a period of positive inspiration pressure extended to pressurize de-recruited lung regions via collateral airways, during an expiratory phase, a reduction from the positive inspiration pressure down to an undershoot pressure, allowing pressure in pressurized de-recruited lung regions to mobilize mucous along main branch airways of the lung, and elevation of pressure from the undershoot pressure to a positive expiratory pressure, before lung volume reaches a breath cycle minimum.

According to some embodiments of the disclosure, including an electronically controllable valve in the handheld unit, configured to be controllable for providing PEP (Positive Expiratory Pressure) maneuvers to the patient via a mouthpiece.

According to some embodiments of the disclosure, including a pulmonary medicine unit configured for dispensing pulmonary medicine under control of the computing unit, wherein the computing unit is arranged to determine whether to control the pulmonary medicine unit to provide pulmonary medicine based on the analysis.

Unless otherwise defined, all technical and/or scientific terms used herein have the same meaning as commonly understood by one of ordinary skill in the art to which the present disclosure pertains. Although methods and materials similar or equivalent to those described herein can be used in the practice or testing of embodiments of the present disclosure, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system" (e.g., a method may be implemented using "computer circuitry"). Furthermore, some embodiments of the present disclosure may take the form of a computer program product embodied in one or more computer readable medium(s) having computer readable program code embodied thereon. Implementation of the method and/or system of some embodiments of the present disclosure can involve performing and/or completing selected tasks manually, automatically, or a combination thereof. Moreover, according to actual instrumentation and equipment of some embodiments of the method and/or system of the present disclosure, several selected tasks could be implemented by hardware, by software or by firmware and/or by a combination thereof, e.g., using an operating system.

For example, hardware for performing selected tasks according to some embodiments of the present disclosure could be implemented as a chip or a circuit. As software, selected tasks according to some embodiments of the present disclosure could be implemented as a plurality of software instructions being executed by a computer using any suitable operating system. In some embodiments of the present disclosure, one or more tasks performed in method and/or by system are performed by a data processor (also referred to herein as a "digital processor", in reference to data processors which operate using groups of digital bits), such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well. Any of these implementations are referred to herein more generally as instances of computer circuitry.

Any combination of one or more computer readable medium(s) may be utilized for some embodiments of the present disclosure. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device. A computer readable storage medium may also contain or store information for use by such a program, for example, data structured in the way it is recorded by the computer readable storage medium so that a computer program can access it as, for example, one or more tables, lists, arrays, data trees, and/or another data structure. Herein a computer readable storage medium which records data in a form retrievable as groups of digital bits is also referred to as a digital memory. It should be understood that a computer readable storage medium, in some embodiments, is optionally also used as a computer writable storage medium, in the case of a computer readable storage medium which is not read-only in nature, and/or in a read-only state.

Herein, a data processor is said to be "configured" to perform data processing actions insofar as it is coupled to a computer readable memory to receive instructions and/or data therefrom, process them, and/or store processing results in the same or another computer readable storage memory. The processing performed (optionally on the data) is specified by the instructions. The act of processing may be referred to additionally or alternatively by one or more other terms; for example: comparing, estimating, determining, calculating, identifying, associating, storing, analyzing, selecting, and/or transforming. For example, in some embodiments, a digital processor receives instructions and data from a digital memory, processes the data according to the instructions, and/or stores processing results in the digital memory. In some embodiments, "providing" processing results comprises one or more of transmitting, storing and/or presenting processing results. Presenting optionally comprises showing on a display, indicating by sound, printing on a printout, or otherwise giving results in a form accessible to human sensory capabilities.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present disclosure may be described below with reference to flowchart illustrations and/or block diagrams of methods, apparatus (systems) and computer program products according to embodiments of the present disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as a medical practitioner, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the present disclosure are herein described, by way of example only, with reference to the accompanying drawings. With specific reference now to the drawings in detail, it is stressed that the particulars shown are by way of example, and for purposes of illustrative discussion of embodiments of the present disclosure. In this regard, the description taken with the drawings makes apparent to those skilled in the art how embodiments of the present disclosure may be practiced.

In the drawings:

FIGS. 13A-13C are charts schematically representing ventilator breath cycle protocols configured to produce recruitment effects within the lungs, according to some embodiments of the present disclosure;

FIG. 14 schematically represents a sequence of ventilator breath cycle protocols, according to some embodiments of the present disclosure;

FIGS. 15A-15D show imaging results of a living pig experimental subject before (FIGS. 15A-15B) and after (FIGS. 15C-15D) administration of a protocol to re-recruit lung regions de-recruited by injection of CF patient sputum, according to some embodiments of the present disclosure.

DESCRIPTION OF SPECIFIC EMBODIMENTS OF THE INVENTION

Figure 1A:
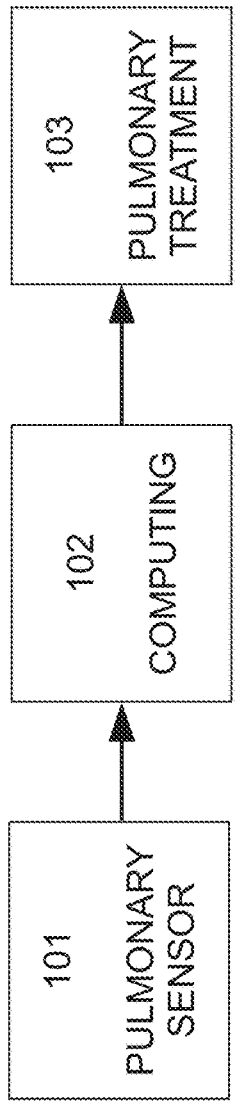
FIGS. 1A-1C are simplified block diagrams of pulmonary treatment and/or medicine administering devices, according to some embodiments of the present disclosure.

The present invention, in some embodiments thereof, relates to a device and methods for treating lung disease; such as, for example, asthma, chronic obstructive pulmonary disease (COPD), pneumonia, acute respiratory distress syndrome, virally-induced lung disease, and/or other obstructive lung diseases treated with the use of a respiratory ventilator.

Introduction

Therapies for lung disease patients include bronchodilators (e.g. Long Acting Beta Agonist (LABA), Long Acting Muscarinic Antagonist (LAMA)), anti-inflammatory medications, oxygen, and non-invasive ventilation. Additional treatments include airway vibration techniques that improve mucus clearance and respiratory physical therapy to improve muscle strength.

Respiratory physical therapy includes maneuvers that increase lung volume. A mechanism of chest physical therapy action comprises enhancement of collateral ventilation (that is, influx of air to lung regions via collateral airways) at higher lung volumes, allowing air to accumulate distal to airways narrowed or obstructed by inflammation and secretions. During coughing and expiration, resultant higher lung volume and increased air pressure in alveoli distal to the airways obstruction promote mucus movement to the more proximal, larger airways.

Respiratory therapy (e.g., in the form of ventilation) may also be provided for patients suffering from pneumonia and/or acute respiratory distress syndrome (ARDS). Such patients may include sufferers from viral pneumonia, for example, due to infection with a coronavirus such as SARS-COV-2, or another virus.

Destruction of normal anatomy of the small airways (including destruction of airway's cartilage which is a major element of airway's stiffness) and the loss of elastic recoil due to the destruction of parenchyma leads to reduced airway and alveolar potency and stability. The result of the above is reduced alveolar recruitment during inspiration and acceleration of premature small airway collapse during normal cough. As disease progresses the premature collapse will appear also during normal expiration. There are two major challenges that amplify each other: The first is premature airway collapse during a cough that leads to an ineffective secretion clearance. As a result, less air reaches the distal airways and the alveoli, this potentially causes low gas exchange in the infected areas and blocks the path for inhaled medication. An inhomogeneous pattern of the lung damage results in an unequal air distribution throughout the lung, meaning that sicker areas are less ventilated than healthier areas. Paradoxically, treating patients with aerosolized medications may prove futile; the healthier parts receiving more medication while the sicker parts hardly receiving medication, or even not at all. This uneven distribution poses the second challenge of delivering medication to the sicker parts of the lung. The interaction between inflammation, tissue destruction and poor secretion clearance potentially leads to a vicious cycle. Poor drug delivery leads to excessive inflammation and mucus production which in turn leads to poor ventilation that leads to poor mucus clearance, consequently reducing the amount of drug delivered.

A lung expansion and airway clearance device is desired, for effective drug delivery into small airways at a patient's home setting or at a hospital, clinic or any other medical facility.

In various aspects of the present invention, various additional beneficial features may be realized, such as one or more of:

An affordable device;
A portable device;
A non-invasive device;
Personalized drug delivery into the small and usually blocked airways;
Treatment repeatable up to several times daily.

Overview

An aspect of some embodiments of the invention relates to one or more of the following:

optionally sensing pulmonary-related data: directly from measured flow and/or volume of exhaled and inhaled gas, indirectly using other sensors, and/or using control input (e.g., input of a healthcare provider and/or patient: voice, manually, or other);

optionally applying one or more of a computing step, computed analysis, algorithm-based analysis, algorithm-based manipulation of the sensed data;

providing physical therapy for opening up distal airways in a lung, in some embodiments optionally at a time based on the computing;

providing medicine, in some embodiments optionally after the physical therapy, in some embodiments optionally at a time and/or duration based on the outcome of the computing step; and collecting data during the sensing and/or the physical therapy and/or the providing medicine.

An aspect of some embodiments of the invention relates to a method and a device for collecting pulmonary data from patients and automatically (e.g. by computer) making a decision on whether to apply pulmonary treatment and applying the treatment.

In some embodiments the computer optionally makes a decision regarding which pre-programmed protocol to apply. In some embodiments, by way of a non-limiting example, a computer estimates patient condition as one of three conditions: mild, moderate and severe.

In some embodiments the computer optionally makes a decision regarding which pre-programmed protocol to apply based on the computer's estimate of the patient's condition.

In some embodiments the computer makes a decision regarding whether to dispense medicine. Optionally the computer decides on a dose of the medicine to dispense.

In some embodiments the computer makes a decision regarding a dosing schedule for providing the medicine; for example, whether to dispense the medicine before, during or after applying the pulmonary treatment.

Optionally, decisions are made based on the impact of the pulmonary physical treatment as indicated by signals collected from sensors; and/or indicated manually, for example, by a command provided by a healthcare provider or patient.

By way of a non-limiting example, in some embodiments the dose and/or dosing schedule (set, for example, automatically by the computer or manually, e.g., by a physician) is optionally according to the dosage prescribed by current best-practice guidelines.

By way of a non-limiting example, in some embodiments the timing of the medicine release is optionally set so that medicine inspiration duration time is 3 seconds.

It is noted that it is expected that typically a first second of a duration of inspiration potentially mainly fills healthy airways. By way of a non-limiting example, in some embodiments the timing of the medicine release is optionally set to start approximately 1 second after beginning of inspiration. By way of a non-limiting example, in some embodiments room air without medicine is optionally provided during the first second of the duration of inspiration.

It is noted that it is expected that typically, after the first second of the duration of inspiration, sick airways start to receive more airflow.

By way of a non-limiting example, in some embodiments the timing of the medicine release is optionally set to start approximately 1 second after beginning of inspiration.

By way of a non-limiting example, in some embodiments medication release is optionally following a 0.5-1.5 seconds delay.

In some embodiments the delay optionally depends on a status of the patient.

In some embodiments a default setting is set for a 1 second delay.

By way of a non-limiting example: in some embodiments, the dose and/or dosing schedule of the medicine provided is according to known medical practice recommendations and/or according to international guidelines.

Additional example pulmonary therapy protocols are also referred to in FIG. 7B, described below.

In some embodiments calculations are optionally based on a desired respiratory rate, in some cases separated into values for an inspiratory phase and values for an expiratory phase.

In some embodiments, the desired optimal respiratory rate is 10-12 liters/minute.

In some embodiments, the desired optimal respiratory rate is 10-12 liters/minute and duration and pressure values are optionally calculated to cause a patient to achieve approximately the desired optimal respiratory rate.

An aspect of some embodiments of the invention relates to a method and a device for collecting pulmonary data from patients and automatically (e.g. by computer) making a decision on whether to dispense medicine and optionally dispensing the medicine. In some embodiments the computer makes a decision on selecting a dose of the medicine to dispense.

In some embodiments the computer makes a decision regarding a dosing schedule for providing the medicine. The dosing schedule may include, for example, whether to dispense the medicine before, during or after applying the pulmonary treatment. In some embodiments, the computer makes a decision regarding whether to provide pulmonary treatment, and optionally during what duration to provide such treatment. In some embodiments the computer makes a decision regarding whether to provide the pulmonary treatment before, during or after providing the medicine.

An aspect of some embodiments of the invention relates to a non-invasive inhalation and lung expansion device for treatment of lung disease patients; for example, asthma, COPD, and/or viral-related lung disease patients.

In some embodiments the device optionally utilizes a therapeutic protocol for expanding or opening up distal airways in a patient's lung.

In some embodiments the device optionally measures physiological parameters of a patient's lung to determine when the patient's lung is ready for applying inhalatory medicine, optionally by sensing when distal airways produce less resistance to airflow.

In some embodiments the device optionally utilizes a therapeutic protocol for synchronized aerosolized drug delivery into the distal airways and/or throughout collateral airways.

In some embodiments the therapeutic protocol includes one or more physical therapy protocol(s) and one or more medication timing protocol(s), which can be asynchronous or synchronous to a patient's physiological cycles, i.e., delivered in a way which may be independent of the patient's natural inspiratory cycle, cardiac cycle or other physiological functions, or dependent upon the patient's natural inspiratory cycle, cardiac cycle or other physiological functions, respectively.

In some embodiments the physical therapy protocol(s) may be applied directly to the mouth of a patient. In some embodiments the physical therapy protocols may be applied through a mouthpiece and/or a mask. In some embodiments the physical therapy protocol(s) may be administered at a predetermined frequency and/or pressure, optionally in a programmed manner, optionally synchronous or asynchronous.

In some embodiments the medication timing protocol(s) may be applied directly to the mouth of a patient. In some embodiments the medication timing protocols may be applied through a mouthpiece and/or a mask. In some embodiments the medication timing protocol(s) may be administered at a predetermined frequency and/or pressure, optionally in a programmed manner, optionally synchronous or asynchronous.

In some embodiments the above-mentioned device uses a sensing mode for analyzing a patient's state within a short time, such as in a range of 2 seconds to 2 minutes, for example in under 60 seconds.

In some embodiments, after causing airways to open up, at least somewhat, and/or after providing pressure to inflate a lung, at least somewhat, optionally during a first phase of the treatment, an amount of secretion is potentially decreased, and airway resistance to flow is potentially reduced. In such embodiments, optionally based on sensing reduced airway resistance, optionally by sensing increased airflow, medicine is optionally delivered. In some embodiments the medicine may include, by way of some non-limiting examples: beta2 and/or antibiotic therapy, bronchodilators (a group including beta2-agonists and anticholinergics), short-acting bronchodilators, corticosteroids, methylxanthines, and/or long-acting bronchodilators; optionally, using a standard dosage.

By way of example, the group of short-acting bronchodilators includes: albuterol, levalbuterol, ipratropium, ibuterol/ipratropium, and the like.

By way of example, the group of corticosteroids includes: Fluticasone, Budesonide, Prednisolone, and the like.

By way of example, the group of long-acting bronchodilators include aclidinium, arformoterol, formoterol, glycopyrrolate, indacaterol, olodaterol, salmeterol, tiotropium, umeclidinium, and the like.

In some embodiments, an inhalative phase is optionally initiated following 2-6 cycles of pre-drug delivery treatment (potentially cleaning and inflating the lungs) determined in accordance with a patient's disease type and/or in accordance with sensing amount of secretion and/or in accordance with sensing airway resistance.

In some embodiments, a pulmonary treatment total duration is optionally set to last 25-30 minutes, or in a range of 5, 10, 15, 20, 25, 30, 35, 40, 45, 50, 55 and 60 minutes, or values therebetween.

In some embodiments, an expectoration phase is optionally set to last 10-15 minutes, or in a range of 2, 5, 10, 15, 20, 25, 30, 35, 40, 45, 50, 55 and 60 minutes, or values therebetween. In some embodiments, the expectoration phase is optionally followed by providing or releasing medicine to the patient's lungs.

In some embodiments the above-mentioned device has an expectoration mode which includes one or more of a physiology based lung inflation capability and a physiology based secretion removal capability.

In some embodiments the above-mentioned protocols can provide a personalized medication dose to a patient.

In some embodiments a personalized medication dose is optionally calculated using a patient's profile. In some embodiments, the patient's profile includes one or more of: background medical condition input by a physician or acquired from a medical database; a patient's demographic data; a patient's physical measurements, vital sign values, clinical parameters such as, by way of some non-limiting examples, forced expiratory volume (FEV1), expiratory force vital capacity (FVC), residual volume capacity (measured, for example, by an example embodiments sensor or by a spirometer, in some embodiments also compared to previous measurements) and pulmonary data optionally measured during a beginning of treatment. In some embodiments a duration of collecting pulmonary data for use in calculating the personalized medication dose is in a range between 1 second and 3 minutes, for example 1 minute. Some non-limiting examples of pulmonary data gathered and optionally used in the calculating of the personalized medication dose include air pressure and air flow rate.

In some embodiments the pulmonary data is optionally measured by sensors included in a device or system of the present invention. The pulmonary data optionally includes one or more of: pressure of air provided to patient, flow velocity of air provided to patient, pressure of air exhaled by the patient, and flow velocity of air exhaled by the patient.

In some embodiments the personalized dose is optionally the dose recommended by standard established medical guidelines or international guidelines, and the personalization of the treatment is optionally by an adjustment of cycle durations.

In some embodiments the above-mentioned device provides a synchronized drug release, optionally with positive pressure.

In some embodiments the above-mentioned device or above-mentioned system acts as a unified system or apparatus, which incorporates both therapeutic treatment (lung expansion and/or collateral ventilation and/or secretion removal and/or airways clearance) and an aerosolized drug delivery protocol.

In some embodiments the above-mentioned device or above-mentioned system or apparatus automatically:

Analyzes pulmonary measurements and produces a statistical analysis and/or a comprehensive report, which is optionally automatically sent to a patient personal file for optional further evaluation and diagnosis by a physician. In some embodiments patients are optionally divided into different categories according to severity of their disease and level of obstruction. In some embodiments, the more severe the patient category the later the release of the medication and/or the higher the dose.

Predetermines drug dosage (e.g., comprising dose and dosing schedule) according to a patient's profile.

Figure 7A:
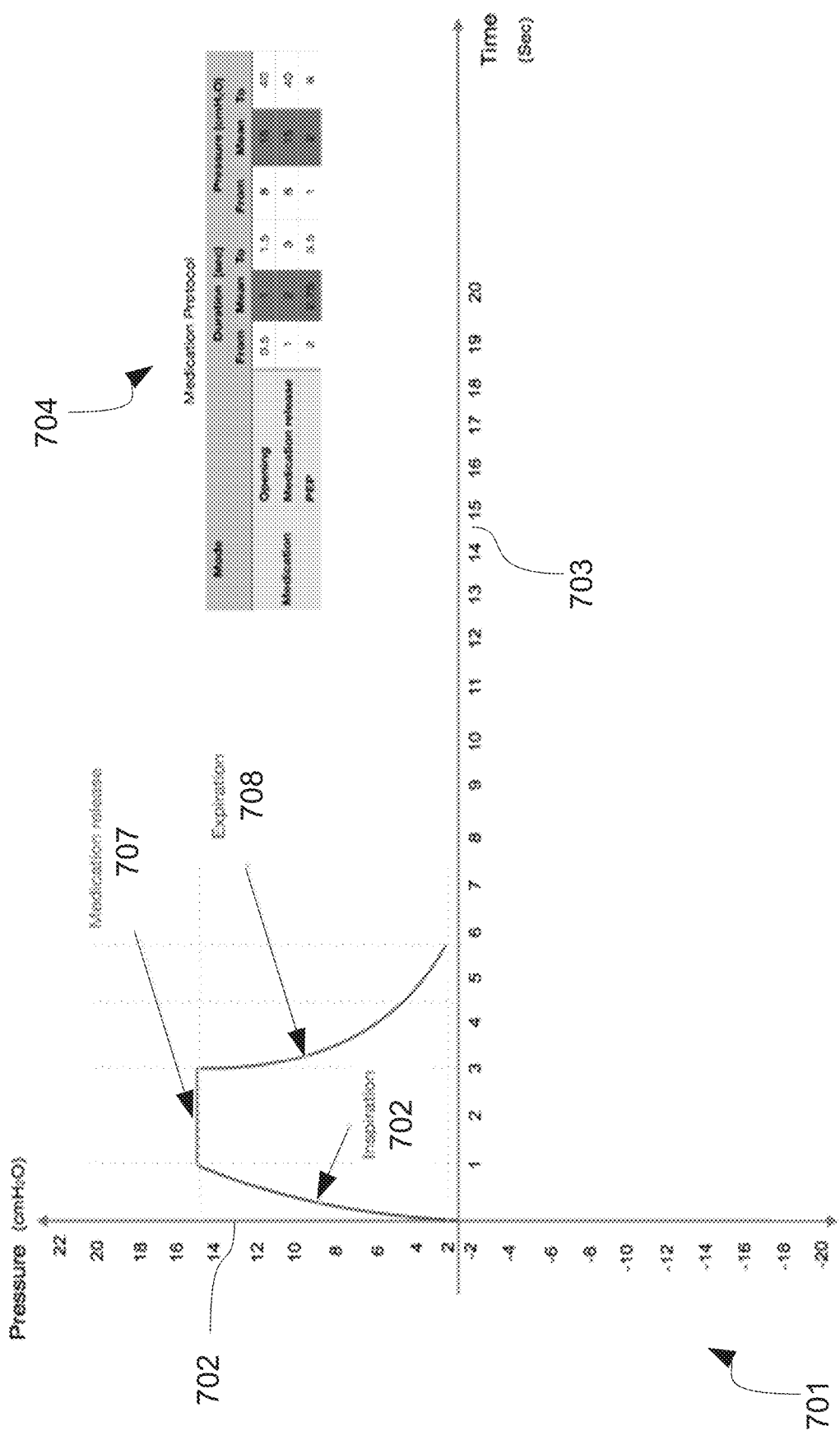
FIG. 7A is a graph illustrating pulmonary therapy, according to some embodiments of the present disclosure.
Figure 7B:
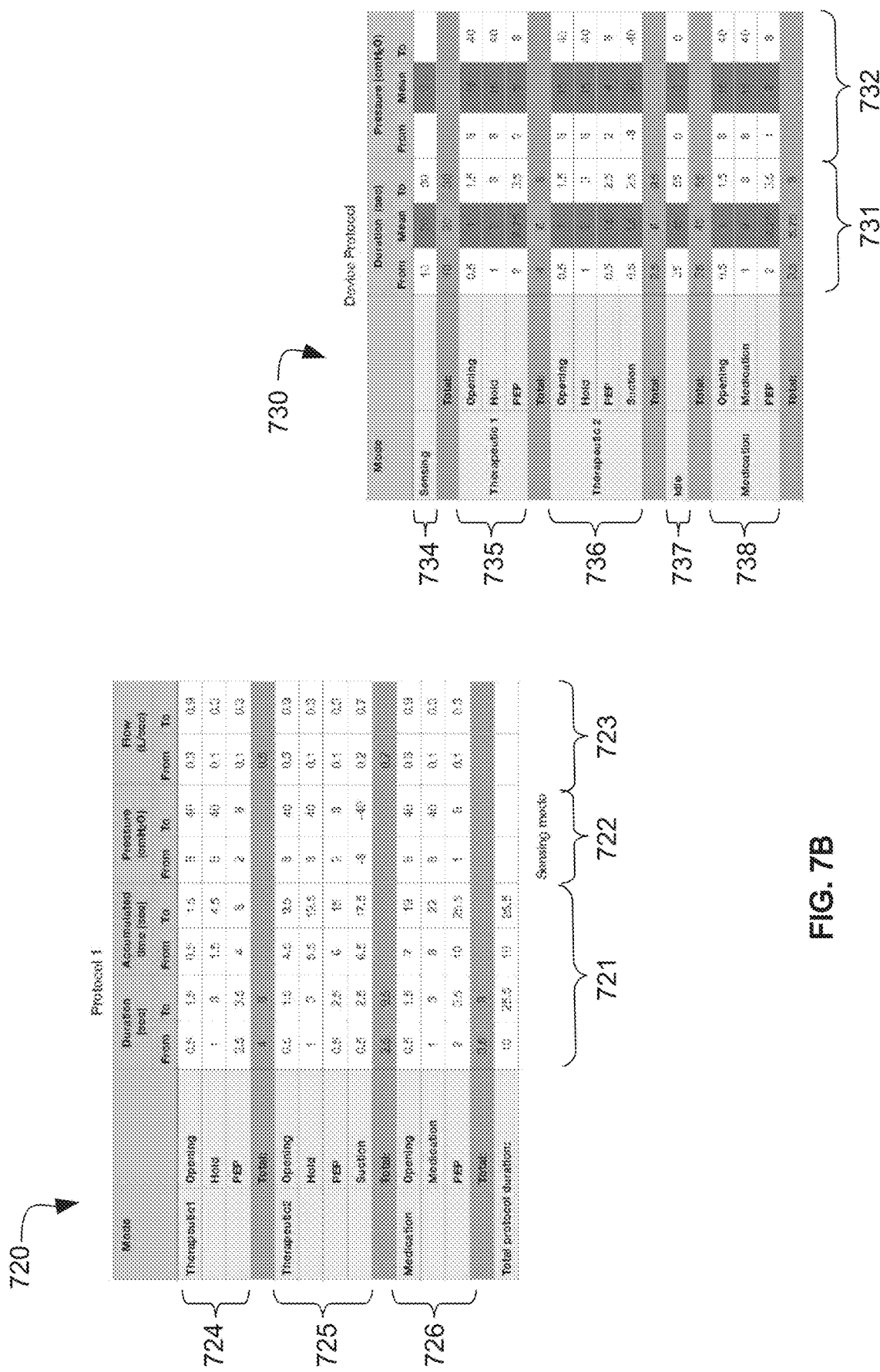
FIG. 7B includes tables illustrating pulmonary therapy, according to some embodiments of the present disclosure.

Some example embodiments of pulmonary therapy protocols are described in FIG. 7B.

Some example embodiments of pulmonary therapy protocols are physiology based.

In some embodiments a desired respiratory rate is 10-12 liters/minute during treatment, at approximately 5-6 seconds per breathing cycle, approximately 2.5-3 seconds for inspirium and the same for approximately 2.5-3 seconds expirium.

In some example embodiments the inspiratory phase is optionally divided into two portions, an opening portion and a hold portion. The division may optionally be used in any one or in all three different modes (inflation, expectoration and medication).

In some embodiments, during an opening portion of the inspiratory phase the healthier parts of the lung are the first to be ventilated, and during the hold portion, the sicker parts are inflated through collateral ventilation. In such embodiments a timing of the medication release is set to be at a beginning of or during the hold portion.

In some embodiments, physiological principles of the lung are optionally used for potentially achieving better inflation and/or better expectoration.

Figure 6:
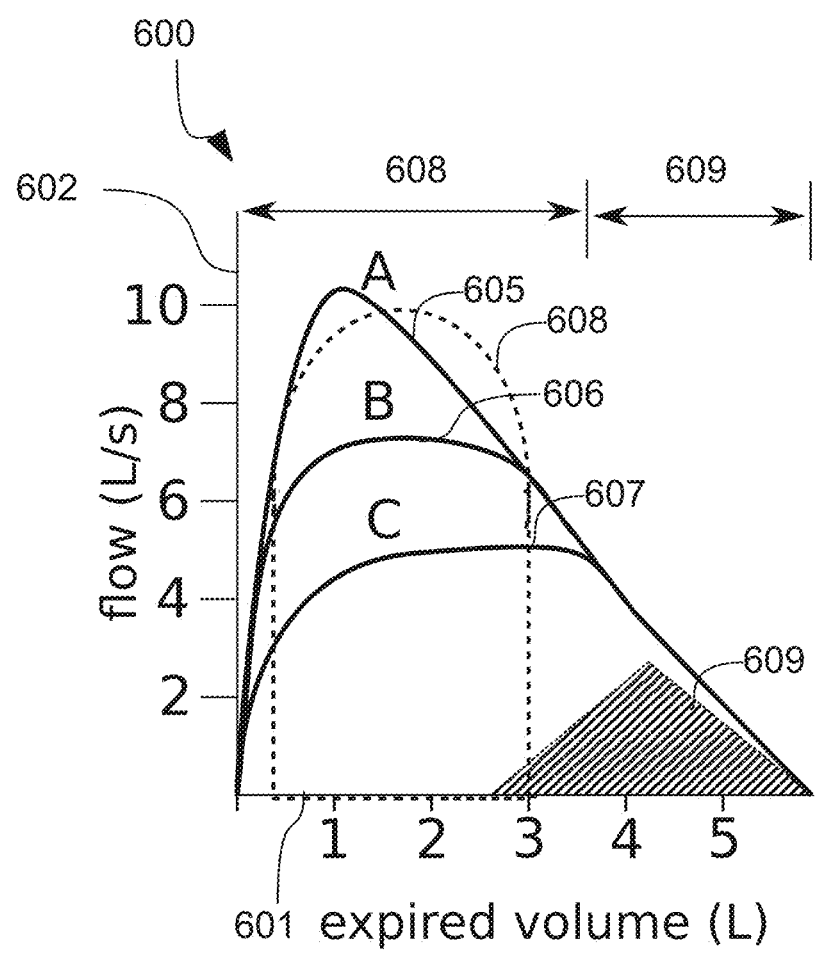
FIG. 6 is a simplified graph illustration of air flow in a lung, according to some embodiments of the present disclosure.

Reference is made to FIG. 6, which shows an example of how expectoration can potentially be provided at a medically appropriate time and/or potentially reach deep and/or distal airways.

Optionally the method or algorithm is stored on a cloud-based server.

In some embodiments the above-mentioned device or above-mentioned system protocol parameters and maneuvers are determined according to a collateral ventilation principle. Effective chest physiotherapy is optionally based on reducing resistance to collateral flow/ventilation, inducing a pressure gradient across the collateral pathways and/or the opening of the collateral pathways for potentially improving ventilation of alveolar structure throughout a network of small air passages that bypass the normal airways.

Asthma, COPD and CF are all characterized by an ongoing, progressive inflammation of the airways, pulmonary vessels, and lung parenchyma, together with impaired secretions clearance, leading to irreversible limitation of airflow.

Lung damage in viral-induced lung disease, for example in viral pneumonia (e.g., as may result in cases of SARS-CoV-2 infection), optionally includes any one or more of: edema, proteinaceous exudate, focal reactive hyperplasia of pneumocytes with patchy inflammatory cellular infiltration and multinucleated giant cells, and alveolar damage. Other associated symptoms include difficulty in breathing, chest tightness, wheezing, and dry cough.

The destruction of the normal anatomy of the small airways and the loss of elastic recoil due to the destruction of parenchyma lead to reduced airway and alveolar potency and stability. The result of the above-mentioned process is reduced alveolar recruitment during inspiration and acceleration of premature small airway collapse during normal cough. As the diseases progresses the premature collapse will appear also during normal expiration.

The proposed system, device, protocol and methods, in some embodiments thereof, provide a one stop shop. Some embodiments potentially offer a combination of effective chest physiotherapy with efficient algorithm-based aerosolized drug delivery. The embodiments potentially offer action based on collateral ventilation, defined as ventilation of alveolar structures through passages or channels that bypass the normal, possibly blocked, airways.

Some embodiments potentially offer evidence-based physiological principles to induce the opening of the collateral passages and the expansion of distal airways. The embodiments potentially use a method of reducing resistance to airflow of collateral airways. Reducing resistance to airflow of collateral airways is potentially achieved by at least one of three maneuvers: (i) deep breath, (ii) hold and (iii) positive expiratory pressure (PEP). By adding positive pressure to the spontaneous inspiration embodiments potentially achieve better inflation of open airways. Alveolar distension potentially retracts the alveolar wall and opens the intra-alveolar pores. The hold maneuver potentially elongates the inspiration time which allows better filling of the lung areas with the lower compliance. Finally, PEP potentially increases airway pressure which potentially generates a relative reduction in the collateral resistance.

In some embodiments the method mentioned above results in better and more equal inflation and consequently better secretion clearance which potentially brings the lungs to an improved state prior to implementing a medication protocol. In some embodiments the medication protocol offers a method of delivering aerosolized drugs. Considering that unhealthy airways in the lung can have delayed opening, the device releases the aerosol only after a delay of, by way of a non-limiting example, 1 second. The aerosol is optionally provided at a positive pressure for a period such as, by way of a non-limiting example, 1.5 seconds, to potentially take advantage of a hold maneuver. In some embodiments a final stage of the medication protocol is expiration against PEP, which potentially sustains the evacuation of the aerosolized drug during expiration.

An aspect of some embodiments of the present disclosure relates to protocols performed by manipulation of pressures supplied by a ventilator and/or another breathing assistance and/or respiratory therapy device to re-recruit lung portions which have de-recruited. In some embodiments, the manipulation of pressures performs a "cough assist" function which helps to recruit de-recruited lung portions and/or helps in expectoration of mucous. Breathing assistance devices used in some embodiments of the present invention comprise devices configured to establish pressure within the lungs according to protocols including pressure values selected from within a range e.g., between about −40 to 50 cm $H_2O$, −20 to 30 cm $H_2O$, or another range of selectable pressures. Pressure may be established, for example, with the use of a sealing mask or other enclosure for the mouth/nose, head, and/or body of the patient; and/or with the use of a tube inserted into airways of the patient.

The terms "respiratory therapy device" and "breathing assistance device" in all their grammatical forms are used throughout the present specification and claims interchangeably with the term "ventilator" and its corresponding grammatical forms, to mean devices such as a respiratory ventilator; a cough simulation device; a cough assistance system; and a mechanical insufflation-exsufflation device.

Optionally, re-recruitment and/or expectoration promoting protocols are performed with a patient with presenting with most or all of a high heart rate, high respiratory rate, low respired volume, high lung resistance, low lung compliance, copious viscous secretions, fatigue, and asymmetrical breathing. Optionally, re-recruitment and/or expectoration promoting protocols are performed with a patient presenting with elevated lung resistance, low chest resistance, poor lung compliance, and copious discharge, but lacking in the other signs just mentioned. In some embodiments, such protocols are provided to a patient in order to promote $CO_2$ exchange.

In some embodiments, an inspiratory hold is performed, which potentially allows time for pressurization of de-recruited lung portions via collateral airways. The duration of the hold is optionally adjusted to target different airway levels preferentially.

In some embodiments, positive expiratory pressure is provided near the end of expiration, which potentially assists in preventing loss of recruitment which may occur at low pressures for recruited lung portions.

In some embodiments, suction is performed during one or more breath cycles to aspirate mucous from the lung, optionally after conditioning to recruit lung portions via collateral airways in a series of one or more previous breath cycles. Potentially, conditioning prior to suction is protective against airway collapse. Potentially, conditioning prior to suction puts the lung in a more recruited state, so that de-recruitment effects which may nevertheless occur due to suction are buffered by an extra reserve of lung capacity. This potentially allows at least some of the desired effects of both collateral pressurization and direct suction to be obtained, by managing their tendency to mutually interfere.

In some embodiments, coughing which is spontaneous and/or elicited by ventilation protocols interrupts the protocol, which optionally resumes after the interruption. In some embodiments, spontaneous coughing itself elicits performance of ventilation protocol(s) to re-recruit lung portions.

Optionally, control is also provided to another pulmonary physical therapy device such as a pressure vest. Optionally, control signals are provided in the form of guidance (e.g., visual and/or auditory guidance) to a human physical therapist working with the patient.

In some embodiments, medicine is given in conjunction with a sequence of mechanically assisted lung portion recruiting and/or expectoration breath cycles; for example, using a pulmonary therapy protocol as described in relation to FIGS. 7A-7B.

In some embodiments, a controller of an existing breathing assistance and/or respiratory therapy device is re-programmed to carry out lung region recruitment and/or expectoration protocols described herein. In some embodiments, a replacement and/or auxiliary controller is provided to an existing breathing assistance and/or respiratory therapy device is re-programmed to carry out lung region recruitment and/or expectoration protocols described herein.

Before explaining at least one embodiment of the present disclosure in detail, it is to be understood that the present disclosure is not necessarily limited in its application to the details of construction and the arrangement of the components and/or methods set forth in the following description and/or illustrated in the drawings. Features described in the current disclosure, including features of the invention, are capable of other embodiments or of being practiced or carried out in various ways.

Example Embodiments

In some embodiments an example device includes a handheld component, for treatment and rehabilitation of patients with chronic supportive pulmonary diseases. In some embodiments an example device also includes an additional base component for providing air under pressure. In some embodiments the handheld component is optionally non-invasive. In some embodiments the device is an inhalation device and/or an airway secretion clearance and/or lung expansion and/or an aerosolized drug delivery device to the small airways of the lung.

Reference is now made to FIG. 1A, which is a simplified block diagram illustration of an example embodiment of the invention.

FIG. 1A shows an example embodiment of a system for collecting pulmonary data from patients and providing pulmonary physical treatment.

The system of FIG. 1A optionally includes a pulmonary sensor 101; a computing unit 102, optionally arranged to receive data measured by the pulmonary sensor 101, optionally analyze the data, optionally produce an analysis; and a pulmonary physical treatment unit 103, optionally for providing pulmonary physical treatment when controlled by the computing unit.

In some embodiments the computing unit 102 is arranged to determine whether to control the pulmonary treatment unit 103 to provide pulmonary physical treatment based on the data.

Figure 1B:
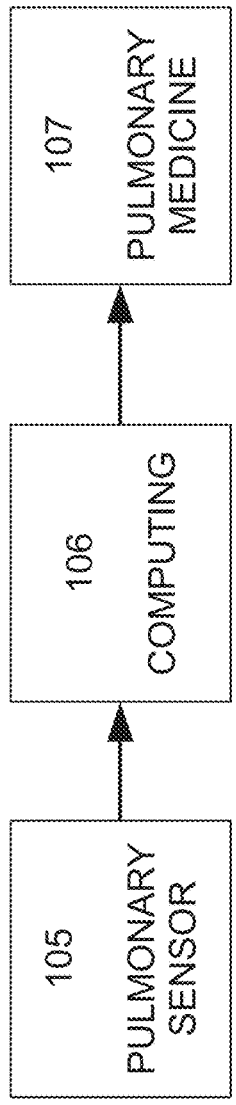

Reference is now made to FIG. 1B, which is a simplified block diagram illustration of an example embodiment of the invention.

FIG. 1B shows an example embodiment of a system for collecting pulmonary data from patients and providing pulmonary medicine.

The system of FIG. 1B optionally includes:
a pulmonary sensor 105;
a computing unit 106, optionally arranged to receive data measured by the pulmonary sensor, optionally analyze the data, optionally produce an analysis; and
a pulmonary medicine unit 107 for dispensing pulmonary medicine.

In some embodiments the computing unit 106 is arranged to determine whether to control the pulmonary medicine unit 107 to provide pulmonary medicine based on the analysis.

Figure 1C:
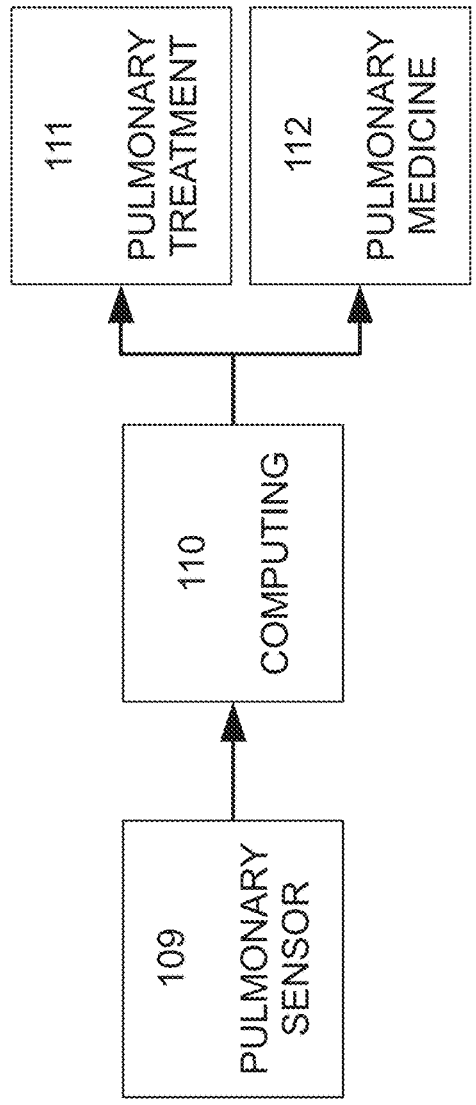

Reference is now made to FIG. 1C, which is a simplified block diagram illustration of an example embodiment of the invention.

FIG. 1C shows an example embodiment of a system for collecting pulmonary data from patients and providing pulmonary physical treatment and/or pulmonary medicine.

The system of FIG. 1C optionally includes:
a pulmonary sensor 109;
a computing unit 110 optionally arranged to receive data measured by the pulmonary sensor, optionally analyze the data, optionally produce an analysis; a pulmonary physical treatment unit 111, optionally for providing pulmonary physical treatment; and a pulmonary medicine unit 112 for dispensing pulmonary medicine.

In some embodiments the computing unit 110 is arranged to determine whether to control the pulmonary treatment unit 111 to provide pulmonary physical treatment, optionally based on the analysis, and/or control the pulmonary medicine unit 112 to dispense pulmonary medicine, optionally based on the analysis.

In some embodiments the computing unit 110 is arranged to determine whether to control the pulmonary treatment unit 111 to provide pulmonary physical treatment optionally based on the analysis and/or control the pulmonary medicine unit 112 to dispense pulmonary medicine before, during and/or following the pulmonary physical treatment, optionally based on the analysis.

Figure 2A:
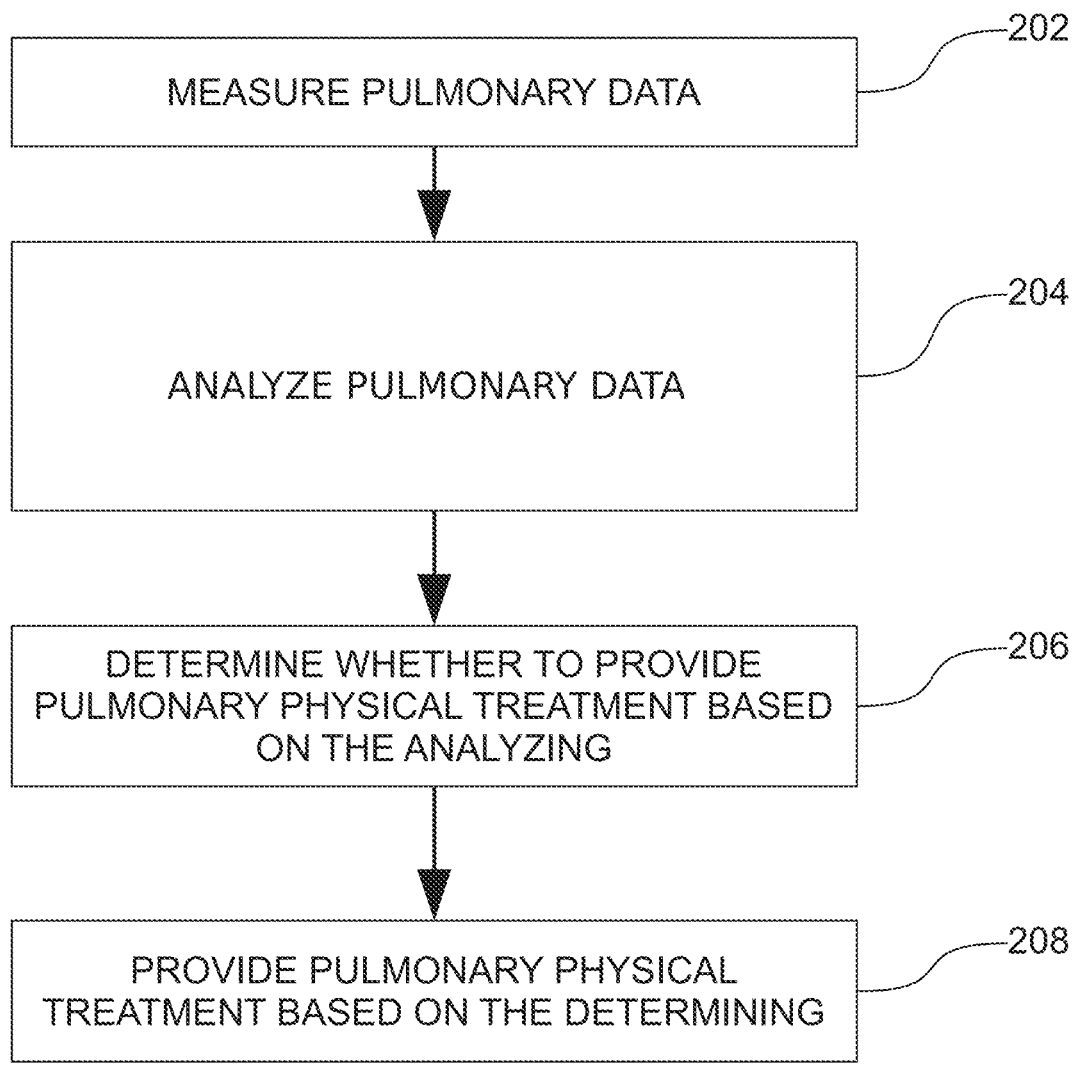
FIGS. 2A-2B are simplified flow charts of methods of operating the devices of FIGS. 1A-1C, according to some embodiments of the present disclosure.

Reference is now made to FIG. 2A, which is a simplified flow chart illustration of an example embodiment of the invention.

FIG. 2A illustrates a method for providing pulmonary physical treatment, the method including:
measuring pulmonary data (202);
using a computing unit to analyzing the pulmonary data (204);
determining whether to provide pulmonary physical treatment based on the analyzing (206); and
providing pulmonary physical treatment based on the determining (208).

Figure 2B:
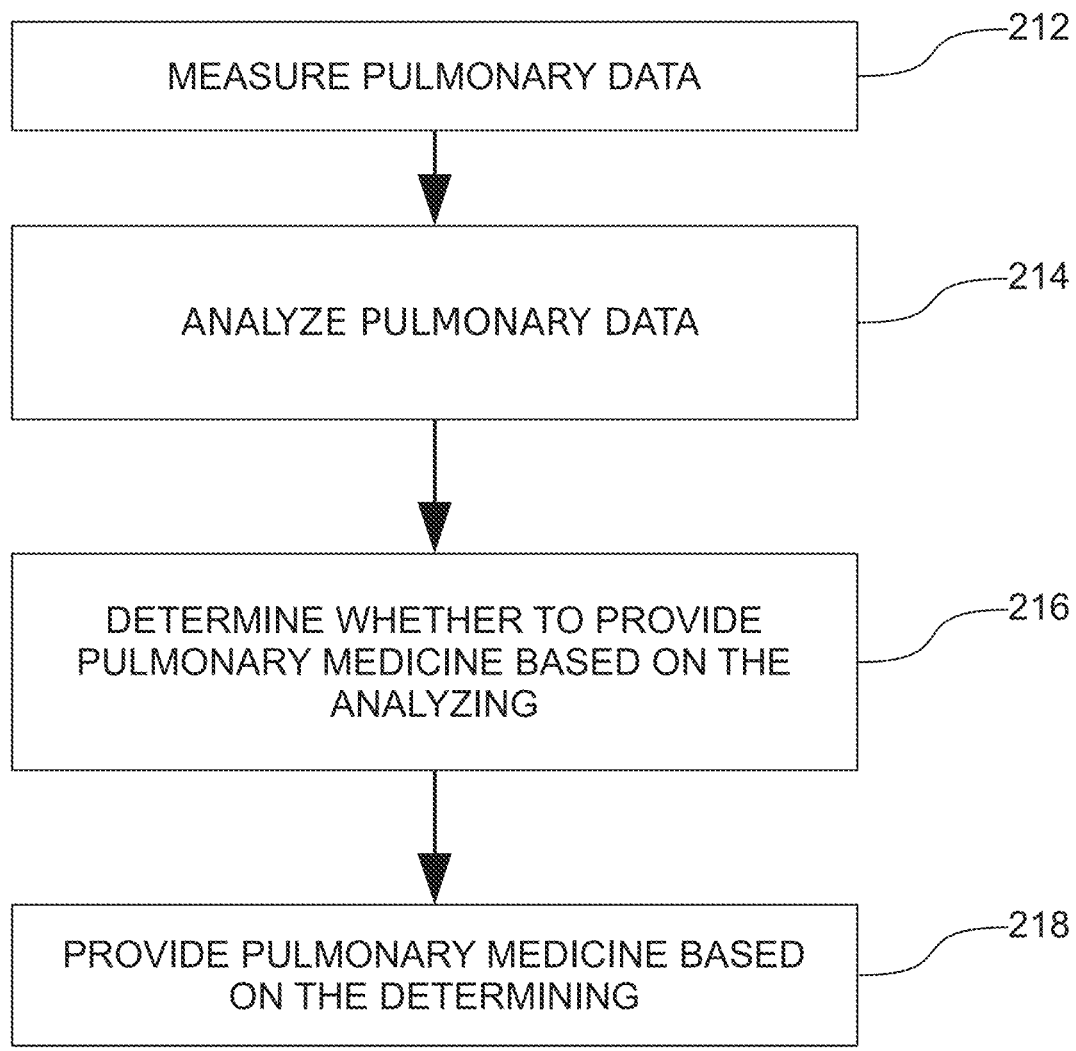

Reference is now made to FIG. 2B, which is a simplified flow chart illustration of an example embodiment of the invention.

FIG. 2B illustrates a method for providing pulmonary medicine, the method including:
measuring pulmonary data (212);
using a computer to analyze the pulmonary data (214);
determining whether to provide pulmonary medicine based on the analyzing (216); and
providing pulmonary medicine based on the determining (218).

Figure 3A:
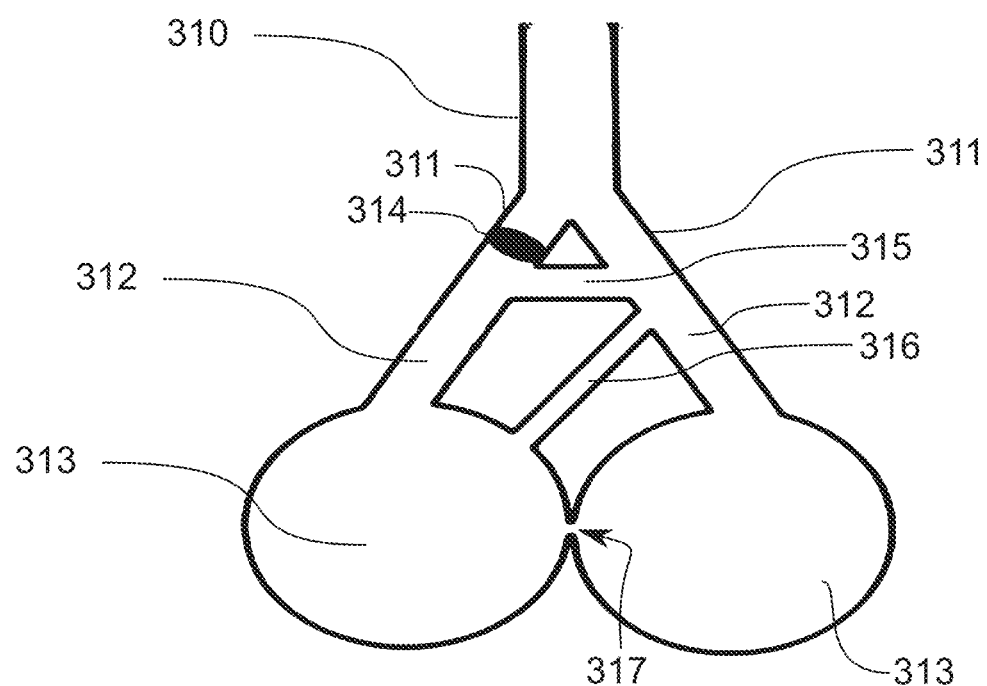
FIGS. 3A-3B are a simplified schematic illustrations of lung structure.

Reference is now made to FIG. 3A, which is a simplified schematic illustration of collateral airways.

FIG. 3A shows a not-to-scale schematic of the lung airways, which are optionally treated by pulmonary physical therapy and/or pulmonary medicine according to some embodiments of the invention.

FIG. 3A shows a trachea 310; bronchi 311; alveolar ducts 312; alveolar sacs 313; a blocked collateral airway 314; an inter-bronchiolar channel of Martin 315; a bronchiole-alveolar channel of Lambert 316; and an inter-alveolar pore of Kohn 317.

In some embodiments a patient optionally uses an example embodiment device 2-3 times a day, optionally on a daily basis, optionally at home and/or in a hospital (or any other medical facility) setting. In some embodiments a duration is up to 20-25 minutes per treatment.

In some embodiments the device optionally operates based on a combination of one or more of the following modes of therapy:
Chest physiotherapy—optionally based on reducing resistance of collateral airways, such as one or more of the inter-bronchiolar channel of Martin 315, the bronchiole-alveolar channel of Lambert 316, and the inter-alveolar pore of Kohn 317 and/or inducing a pressure gradient across the collateral airways. In some embodiments the chest physiotherapy optionally produces dilating forces which potentially help reopening collapsed airways and opening the collateral pathways, for potentially improving ventilation of alveolar structure throughout a network of small air passages that bypass normal airways.

Reducing a collapse of small airways during expiration—optionally utilizing PEP (Positive Expiratory Pressure) maneuvers and potentially improving and/or enabling an escape of air on expiration, bypassing collapsed small airways, thereby reducing one or both of resting and/or dynamic hyperinflation.

Providing aerosolized drug delivery, deep into the sicker parts of the lung, optionally utilizing a positive air pressure at a specific timing during the treatment. In some embodiments the positive air pressure is optionally provided after cyclic therapeutic pulses, which potentially encourage secretion removal and coughing, which potentially produce a condition for delivering the aerosolized drug into the small airways.

Figure 3B:
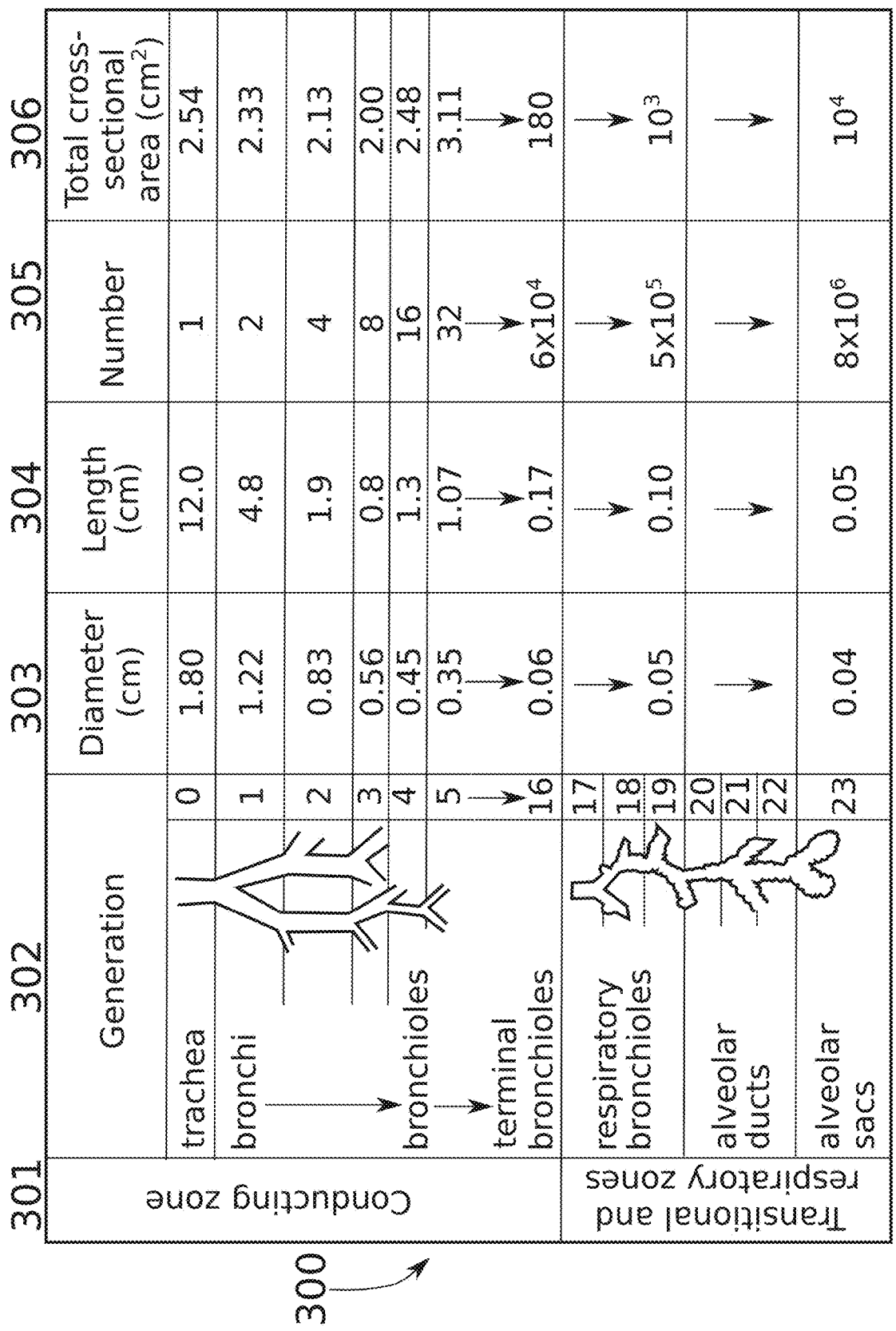

Reference is now made to FIG. 3B, which is a simplified illustration of information describing lung structure.

FIG. 3B shows a table 300 which provides information describing lung structure.

Table 300 includes:
- a first column 301, which describes whether a lung component in the table 300 is in a conduction zone or a transitional and respiratory zone;
- a second column 302, which names lung components and numbers generations from 0 on up, proportional to a degree of branching;
- a third column 303 which provides a typical diameter, in centimeters, of the lung components;
- a fourth column 304 which provides a typical length, in centimeters, of the lung components;
- a fifth column 305 which provides a number of the lung components in a lung; and
- a sixth column 306 which provides a total cross-sectional area, in square centimeters, of the lung components.

In some embodiments the device includes preprogrammed operations, including one or more of the following modes of operation:

A sensing mode—sensing breathing and/or sensing lung condition: During a patient's tidal breathing, the device senses base-line breathing cycles using a device such as a spirometer, an audio signal breathing sensor or by other means such as $CO_2$ sensors and/or NO sensors, the sensors are used for optionally sensing inhalation and/or exhalation stages of the patient's respiratory cycles, such as expiratory and/or inspiratory timing and/or rate and/or ratio, and/or lung compliance evaluation.

In some embodiments, during the breathing sensing mode, the device provides no air pressure to the patient.

In some embodiments a patient's lung condition is optionally manually defined in the system by a physician, a caretaker, or even the patient, before a first treatment, so that a programmed treatment method automatically adjusts treatment parameters and protocol, considering the patient's physiological condition.

In some embodiments a programmed treatment method automatically adjusts treatment parameters and protocol according to accumulated patient records during the sensing mode.

In some embodiments the patient's data condition and collected measurements during sensing mode are optionally used as input to a machine learning module, which optionally personalizes and adjusts one or more of: a number of pressure pulses, a pressure of pressure pulses, number of therapeutic cycles, a synchronization of intermittent ventilation, PEP, suction, dose, and/or dosing schedule of aerosolized medication.

In some embodiments the device can provide a different sequence of therapeutic protocol on inhalation vs. exhalation.

In some embodiments different patient conditions are optionally treated by different protocols, of which each one of the different protocols may have a set of sequences of protocols according to lung compliance and/or subject condition.

In some embodiments the device and/or sensor optionally collect a patient's data, producing a database that contains data such as lung compliance, adherence to medication treatment, patient compliance and efficacy of treatment.

First Example Therapeutic Mode

Figure 4:
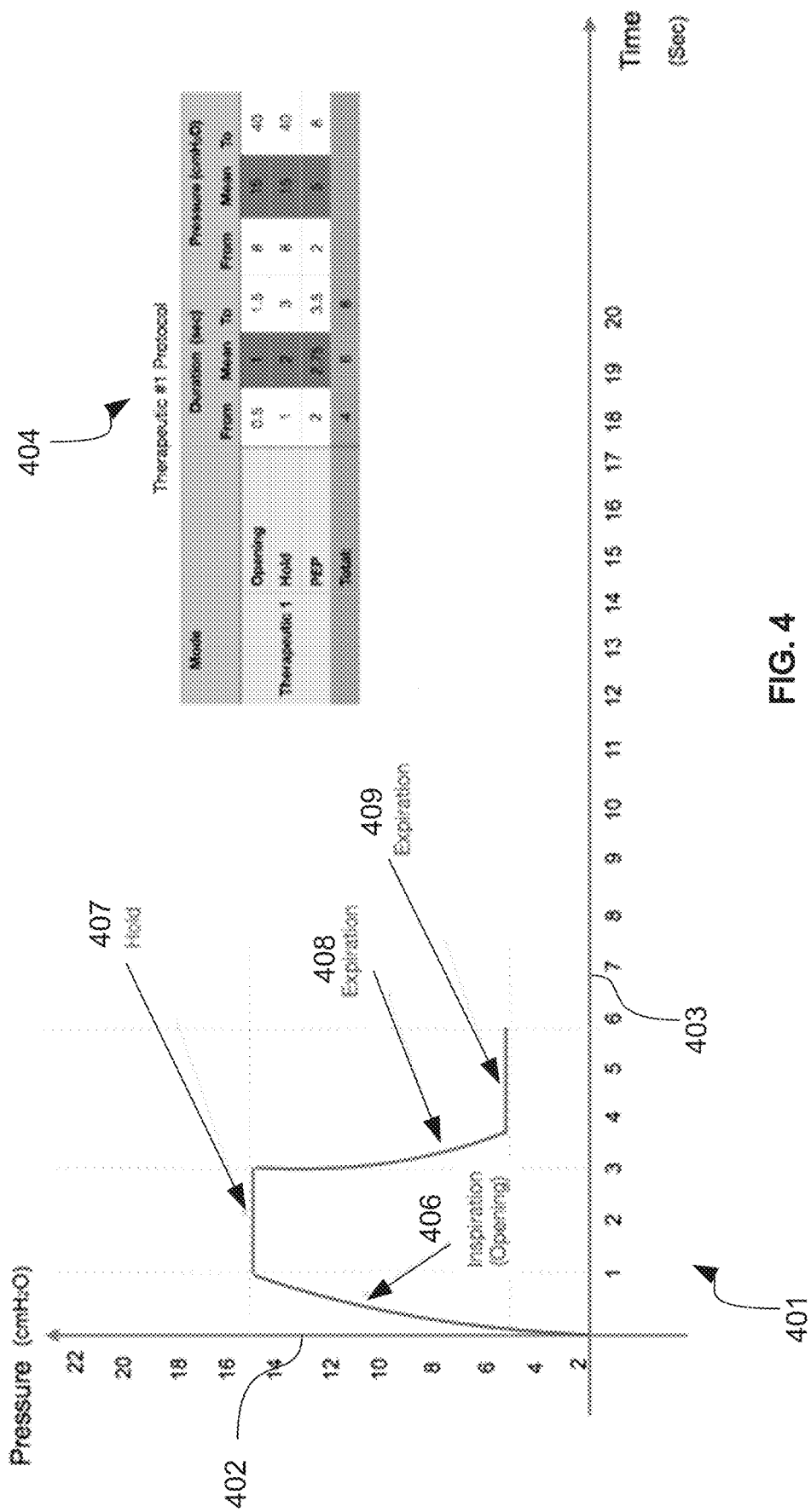
FIGS. 4 and 5 are graphs illustrating pulmonary therapy, according to some embodiments of the present disclosure.

Reference is now made to FIG. 4, which is a graph illustrating pulmonary therapy according to an example embodiment of the invention.

FIG. 4 illustrates a first therapeutic mode (also referred to as "therapeutic mode 1").

FIG. 4 includes a graph 401 and a table 404.

The graph 401 has an X-axis 403 showing time, in seconds, a Y-axis 402 showing pressure in centimeters of $H_2O$. The graph 401 shows periods in a timeline corresponding to different periods in the first therapeutic mode.

The graph 401 shows an inspiration period 406, a hold period 407, a first expiration period 408 and a second expiration period 409.

In some embodiments the first expiration period 408 optionally includes PEP (Positive Expiratory Pressure).

In some embodiments the second expiration period 409 optionally includes constant positive pressure.

In some embodiments a burst of positive pressure pulse up to $8\text{-}40\ cm\ H_2\text{-}O$ is provided for a duration of a patient's inspiratory breathing cycle. A value of the pressure pulse is optionally determined according to one or more measured values of the patient lung compliance, such as, by way of some non-limiting examples, volume of inspiration and pressure during inspiration. In some embodiments lung compliance is measured as volume divided by pressure.

In some embodiments a positive pressure pulse added during inspiration potentially induces a better ventilation of open airways, potentially overcoming small airways' resistance.

In some embodiments, when pressure reaches its desired value, the device maintains the pressure value for a specific duration, for example of 1-3 seconds. This pressure maintenance, termed the hold period 407, extends the inspiration time and potentially reduces resistance to collateral flow/ventilation.

The "Hold" maneuver potentially reduces a pressure gradient across the collateral pathways and potentially induces better distribution and ventilation beyond obstructed airways, and/or by allowing a longer time for the opening of the collateral airways, potentially leading to an opening of the collateral channels for improving ventilation of alveolar structure. This potentially induces alveolar distention that retracts the alveolar wall and potentially induces an opening of the intra-alveolar pores, potentially leading to an enhancement of lung volume, potentially including previously blocked areas.

In some embodiments an adjustable valve/orifice flow resistor optionally determines a PEP value according to the patient's condition, optionally determined based on values measured during the breathing sensing mode and/or the patient expiratory pressure measurements. The PEP maneuver potentially increases the air pressure beyond mucus plugs, potentially reduces collateral airway resistance and potentially opens the collateral airways, potentially prevents airway collapse of sick airways, potentially allows mucus transport from distal airways to more proximal airways. The PEP maneuver potentially causes elongation of a duration of expirium, potentially improves ventilation, and potentially reduces $CO_2$ levels in the alveoli, which potentially improves a patient's subjective feeling of dyspnea.

In some embodiments, during 10-25% of a patient's exhale phase, the device optionally provides descending air pressure until reaching a pressure of, for example, 2-8 cm $H_2O$. In some embodiments the pressure is optionally kept constant for a few seconds, optionally until commencing of a next consecutive pulse.

In some embodiments intermittent pulses of therapeutic mode 1 can optionally be applied in a sequence of several repetitive cycles.

In some embodiments the device action is based on lung physiology. Flow is optionally determined by an airway radius, pressure gradient, length of the airway and viscosity of the medium, for example as defined by the Poiseuille equation:

$$Q = \frac{\pi r^4}{8\eta} \cdot \frac{\Delta P}{L} \qquad \text{Equation 1}$$

Where r is a radius of a tube, η is a coefficient of viscosity, L is a length of the tube, and ΔP is a pressure difference between ends of the tube.

In some embodiments, the device optionally delivers positive pressure producing a gradient sufficient for lung expansion. In some embodiments, in order to potentially make lung expansion more efficient, the "hold" maneuver is optionally used, which potentially provides some major advantages; first, airways with lower compliance (sicker airways) and higher resistance (e.g., reliant on collateral ventilation) will have more time to be inflated; second, by providing constant pressure to a relatively inflated lung, flow is provided at lower velocity, which according to Reynolds number equation, $$\text{Re} = \frac{\rho V D}{\mu}$$

potentially produces laminar flow rather than turbulent flow.

Second Example Therapeutic Mode

Figure 5:
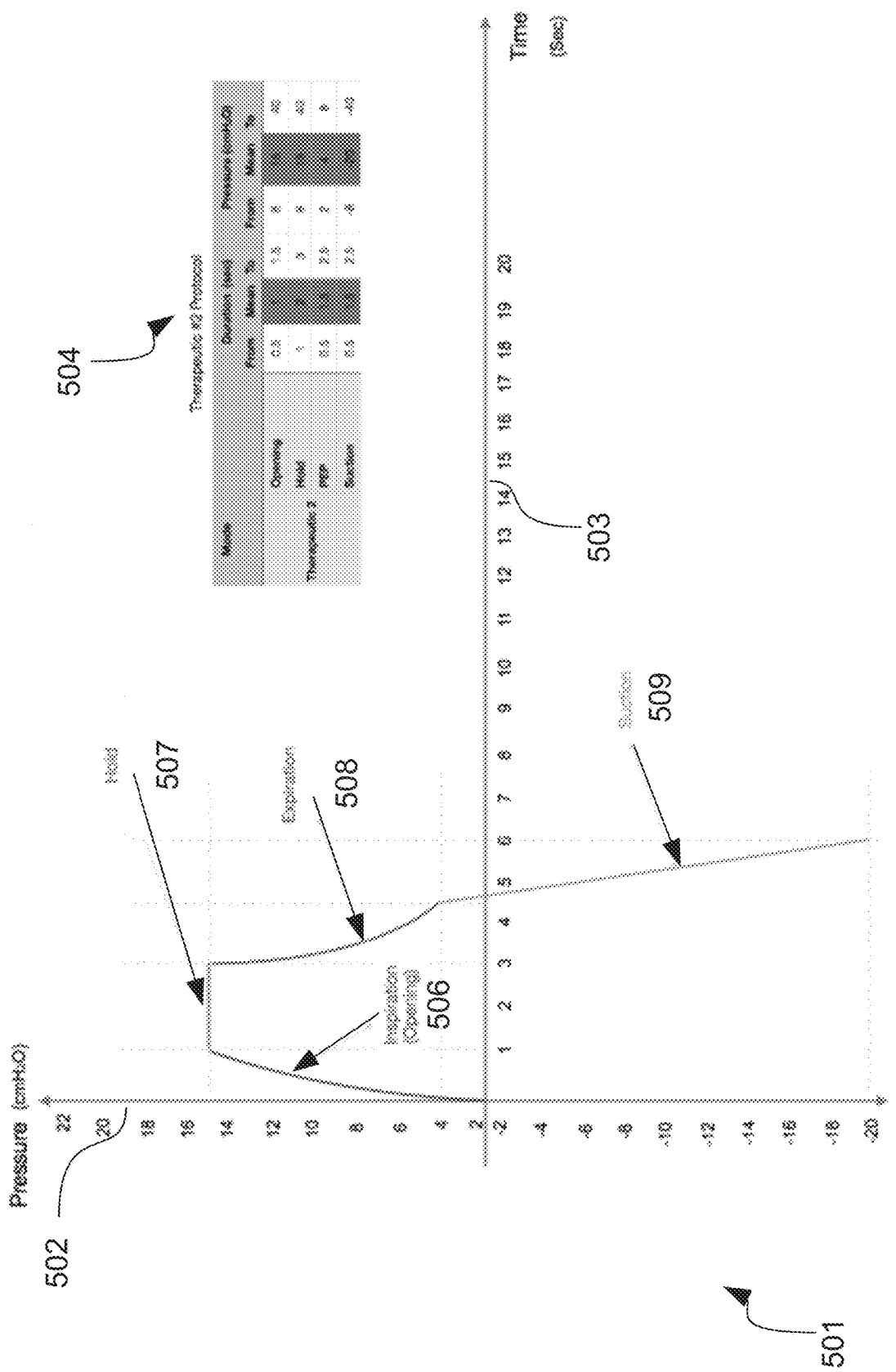

Reference is now made to FIG. 5, which is a graph illustrating pulmonary therapy according to an example embodiment of the invention.

FIG. 5 illustrates a second therapeutic mode (also referred to as "therapeutic mode 2").

FIG. 5 includes a graph 501 and a table 504.

The graph 501 has an X-axis 503 showing time, in seconds, a Y-axis 502 showing pressure in centimeters of $H_2O$. The graph 501 shows periods in a timeline corresponding to different periods in the second therapeutic mode.

The graph 501 shows an inspiration period 506, a hold period 507, a first expiration period 508 and a second expiration period 509.

In some embodiments the first expiration period 508 optionally includes PEP (Positive Expiratory Pressure).

In some embodiments the second expiration period 509 optionally includes suction, which corresponds to negative pressure.

In some embodiments a burst of positive pressure pulse up to $8\text{-}40_{cm\ H2}$~O is provided for a duration of a patient's inspiratory breathing cycle. A value of the pressure pulse is optionally determined according to the patient lung compliance.

In some embodiments a positive pressure pulse added during inspiration potentially induces a better ventilation of open airways, potentially overcoming small airways' resistance.

In some embodiments, when pressure reaches its desired value, the device maintains the pressure value for a specific duration, for example of 1-3 seconds. This pressure maintenance, termed the hold period 507, extends the inspiration time and potentially reduces resistance to collateral flow/ventilation and potentially enables sicker airways with lower compliance to be opened.

The "Hold" maneuver potentially reduces a pressure gradient across the collateral pathways and potentially induces better distribution and ventilation beyond obstructed airways, in some embodiments by allowing a longer time for the opening of the collateral airways, potentially leading to an opening of the collateral channels for improving ventilation of alveolar structure. This potentially induces alveolar distention that retracts the alveolar wall and potentially induces an opening of the intra-alveolar pores, potentially leading to an enhancement of lung volume.

In some embodiments an adjustable valve/orifice flow resistor optionally determines a PEP value according to the patient's condition, optionally determined based on values measured during the breathing sensing mode and/or the patient expiratory pressure measurements. The PEP maneuver potentially increases air pressure beyond mucus plugs, potentially reduces airway resistance of collateral airways, potentially opens the collateral airways, potentially prevents airway collapse of sick airways, and potentially enables mucus transport from distal airways to more proximal airways. In some embodiments the PEP maneuver includes an elongation of duration of expirium, potentially improves ventilation, and potentially reduces $CO_2$ level in the alveoli, which potentially improves a patient's subjective feeling of dyspnea.

In some embodiments, during 10-25% of a patient's exhale phase, the device optionally provides descending air pressure until reaching a pressure of, for example, 2-8 cm $H_2O$. In some embodiments the pressure is optionally kept constant for a few seconds, optionally until commencing of a next consecutive pulse.

In some embodiments intermittent pulses of therapeutic mode 2 can optionally be applied in a sequence of several repetitive cycles.

In some embodiments the device action is based on lung physiology and the formulae described above with reference to therapeutic mode 1 and/or FIG. 4.

In some embodiments, during approximately 10-25% of patient's exhale phase, the device provides descending air pressure until it reaches to a pressure of approximately 2-8 cm $H_2O$, and at the last approximately 75% of the exhale phase, the pressure changes to a negative pressure value of approximately −8 to −40 cm $H_2O$ (suction), to support removal of secretions and/or mucus, potentially during coughing, lasting approximately 0.5-2.5 seconds.

In some embodiments intermittent pulses of therapeutic mode 2 are optionally applied in a sequence of several repetitive cycles.

Reference is now made to FIG. 6, which is a simplified graph illustration of air flow in a lung according to an example embodiment of the invention.

FIG. 6 shows a graph 600 having an X-axis 601 using units of volume (Liters) and a Y-axis 602 using units of volume per second (Liters per second).

FIG. 6 shows three flow curves 605 606 607.

FIG. 6 also shows two areas, a first area 608 and a second area 609. The first area 608 illustrates a period of potential airway collapsibility and the second area 609 illustrates what is termed an independent zone where the airways do not collapse.

FIG. 6 shows that expirium in a lung can be divided to two phases, an effort dependent phase 608 and an independent phase 609. Airway collapse typically occurs in the first, effort dependent phase 608 while the second, independent phase 609 is similar in all flow curves 605 606 607. The three flow curves 605 606 607 show different efforts in breathing, and the three flow curves demonstrate that they all end with an independent phase 609 where airways do not collapse.

In some embodiments a device provides PEP during the first phase 608, thereby preventing premature airway collapse. In some embodiments a negative pressure (suction) is optionally generated during the second phase 609 in order to accelerate clearance of secretions.

Example Idle Mode

In some embodiments, following one or more therapeutic cycles, such as one or more of the therapeutic cycles of mode 1, or mode 2, or a mix of the two modes, a treatment device or a treatment method enters into an idle mode. The idle mode means that air is not provided at a pressure into the lungs and also suction is not applied.

In some embodiments the idle mode lasts a short period of time and a mouthpiece or an air hose are not removed from a patient's face during the idle mode.

In some embodiments the idle mode is optionally a rest mode, and the mouthpiece is optionally removed.

In some embodiments an air hose is removed from a patient's face during the idle mode.

In some embodiments a mouthpiece is removed from a patient's face during the idle mode.

In some embodiments the above-mentioned therapeutic cycles are provided for a duration of, by way of a non-limiting example, 5 to 15 minutes. In some embodiments the above-mentioned therapeutic cycles are provided for a duration in a range from 1 minute to 30 minutes.

In some embodiments the idle mode lasts for, by way of a non-limiting example, approximately 35-55 seconds. In some embodiments the idle mode lasts for a duration in a range from 3 seconds to 3 minutes.

In some embodiments the idle mode serves for allowing the airways to exit from a state of turbulent flow and/or to diminish vibration in the respiratory system, caused by cyclic pressure and/or suction pulses and/or patient coughing. The resting time is potentially used to bring the respiratory system to a condition which allows efficient absorption of a drug into the lungs.

Example Medication Mode

Reference is now made to FIG. 7A, which is a graph illustrating pulmonary therapy according to an example embodiment of the invention.

FIG. 7A illustrates a medication mode.

FIG. 7A includes a graph 701 and a table 704.

The graph 701 has an X-axis 703 showing time, in seconds, a Y-axis 702 showing pressure in centimeters of $H_2O$. The graph 701 shows periods in a timeline corresponding to different periods in pulmonary therapy.

The graph 701 shows an inspiration period 706, a hold period 707, and an expiration period 708.

In some embodiments the inspiration period 706 optionally includes an opening of small lung airways.

In some embodiments the hold period 707 optionally includes application of medicine to the lungs. In some embodiments the application of medicine to the lungs is an application of aerosol medicine to the lungs.

In some embodiments the expiration period 708 optionally includes PEP (Positive Expiratory Pressure).

In some embodiments the second expiration period 509 optionally includes suction, which corresponds to negative pressure.

In some embodiments, following one or more therapeutic maneuvers, which potentially cause airways to be cleared from secretion and mucus, the lungs are now in a good condition which enables to more efficiently deliver an aerosolized drug into collateral pathways and small airways.

In some embodiments the medication mode starts with a burst of positive air pressure, by way of a non-limiting example in a range of approximately 8-40 cm $H_2O$.

In some embodiments the medication mode optionally starts with a delay relative to a beginning of the hold period 707, taking into account that obstructed airways may have a delayed opening. In some embodiments the device optionally releases the aerosolized drug 0.5-1.5 seconds following a beginning of the hold period 707. In some embodiments the device optionally releases the aerosolized drug at a time following a beginning of the hold period 707, the time being in a range between 0 seconds (immediately) and 3 seconds.

In some embodiments the medication is optionally released during a duration of approximately 1-3 sec.

In some embodiments the medication is released while optionally keeping a positive pressure, by way of a non-limiting example, in a range of 8-40 cm $H_2O$. It is believed that the "hold" maneuver while releasing the drug potentially extends inspiration time and/or reduces resistance to collateral flow/ventilation and/or increases drug delivery in a more effective manner, potentially deeper into small airways.

During the hold/medication release maneuver, the aerosolized drug penetrates into the lung and reaches to the obstructed airways through the collateral channels during patient inhalation, which leads to a more effective drug treatment.

In some embodiments, drug dosage (comprising dose and/or dosing schedule) is optionally pre-determined by programming of a computing unit in an example embodiment device.

In some embodiments, drug dosage (comprising dose and/or dosing schedule) is optionally pre-determined by programming of a computing unit according to patient compliance and/or condition.

In some embodiments the patient's condition is optionally determined by a last lung function test such as, by way of some non-limiting examples, expiration in a first second of forced expiration (FEV1), respiratory rate, oxygen saturation in room air, and age.

In some embodiments compliance is optionally determined by a frequency of treatments and/or usage of medications.

In some embodiments compliance is optionally measured according to a number of treatment uses per day.

In some embodiments compliance data is optionally stored for use by the device algorithm.

In some embodiments patient condition and lung compliance are optionally measured on daily basis, optionally measuring volume and pressure.

In some embodiments additional tests are optionally carried out by a lab and optionally stored in the system, in order to potentially pre-determine a pulmonary physical treatment and/or pulmonary medicine protocol In some embodiments a final stage of a medication phase optionally includes patient expiration against PEP maneuver for duration of, by way of a non-limiting example, approximately 0.5, 1, 1.5, 2, 2.5.3, 3.5, 4, 4.5, 5, 5.5, 6, 6.5, 7, 7.5, 8, 8.5, 9, 9.5 or 10 seconds, or values therebetween.

In some embodiments the final stage of the medication phase optionally includes performing under descending positive pressure in a range of, by way of a non-limiting example, approximately 1-8 cm $H_2O$, potentially sustaining an opening and preventing a collapse of small airways during patient exhalation.

In some embodiments such pulses of medication mode can be applied in a sequence of several repetitive cycles.

In some embodiments the pulses of medication mode are optionally applied intermittently.

Table 704 shows a non-limiting example of a medication protocol, including non-limiting example durations and pressures for the example medication protocol.

An example daily treatment protocol by an example embodiment of a pulmonary treatment device Reference is now made to FIG. 7B, which includes tables 720 and 730 illustrating pulmonary therapy according to example embodiments of the invention.

Table 720 shows values of time 721, pressure 722 and flow 723 for a protocol including, for example, inflation 724, expectoration (therapeutic) 725 and medication 726 in an example embodiment of a pulmonary therapy protocol.

Table 730 shows values of time 731 and pressure 732 for a protocol including, for example, an optional sensing period 734, inflation 735, expectoration (therapeutic) 736, an optional idle period 737 and medication 738 in an example embodiment of a pulmonary therapy protocol.

In some embodiments, an example or typical daily treatment optionally includes 2-4 treatments with a duration of 20 minutes each treatment, and a resting time of approximately 3 hours between each treatment.

In some embodiments, each treatment includes a sequence of cycles of the first therapeutic mode, followed by a sequence of cycles of the second therapeutic mode, an idle time of 35-55 seconds, followed by a sequence of cycles of the medication mode.

In some embodiments each one of the therapeutic and medication modes can also be activated separately, or in combinations of two or more modes.

Figure 8:
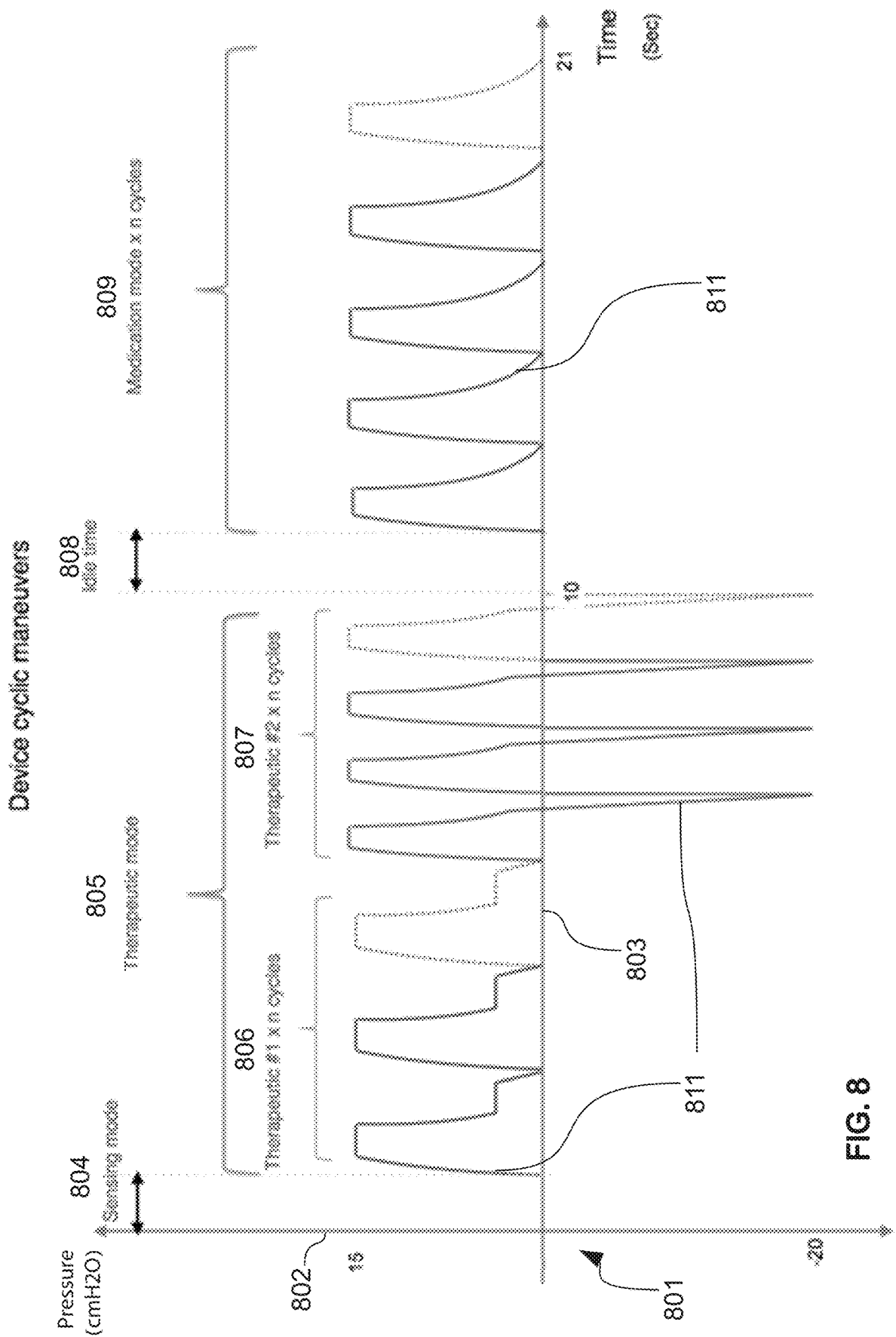
FIG. 8 is a graph illustrating an example pulmonary therapy, according to some embodiments of the present disclosure.

Reference is now made to FIG. 8, which is a graph illustrating an example pulmonary therapy according to an example embodiment of the invention.

FIG. 8 illustrates an example treatment protocol extending over several treatment modes.

FIG. 8 includes a graph 801, having an X-axis 803 showing time, in seconds, and a Y-axis 802 showing pressure in centimeters of $H_2O$. The graph 801 shows a line 811 showing a development of pressure over time elapsed in the example treatment protocol.

The graph 801 shows a first sensing period 804, a therapeutic period 805, an idle period 808, and a medication period 809.

In some embodiments the first sensing period 804 optionally lasts between 0.1 seconds and several seconds, by way of a non-limiting example 1 second. In some embodiments the first sensing period 804 optionally lasts as long as useful for taking measurements and/or analyzing the measurements.

In some embodiments the sensing period lasts between 5 or 10 seconds and 30 seconds, a minute, two minutes, or even up to 5 minutes.

In some embodiments the therapeutic period 805 optionally follows the first sensing period 804. In some embodiments the therapeutic period 805 optionally includes one or more cycles of the first therapeutic mode 806 and/or one or more cycles of the second therapeutic mode 807; optionally in any order between cycles of the first therapeutic mode 806 and cycles of the second therapeutic mode 807 and/or interspersed in any order of groups of one or more cycles of the first therapeutic mode 806 and/or one or more cycles of the second therapeutic mode 807.

In some embodiments the therapeutic period 805 optionally lasts for a duration between 1 second and several seconds, by way of a non-limiting example a duration of 9 seconds.

In some embodiments the therapeutic period 805 optionally lasts as long as useful for improving the lung condition, for example by improving air flow through small airways and/or opening up at least some small airways.

In some embodiments the therapeutic period 805 optionally lasts as long as useful for improving the lung condition.

In some embodiments an improvement of the lung condition is optionally detected, for example by measuring and/or sensing the improvement.

In some embodiments an improvement of the lung condition is optionally detected by measuring and optionally tracking one or more measures such as, by way of some non-limiting examples, a rate of expiration, a rate of inspiration, a duration of expiration, a duration of inspiration, and mathematical functions such as ratios of the previously mentioned values.

In some embodiments an improvement of the lung condition is optionally detected by measuring and optionally tracking one or more measures during the sensing mode, such as, by way of some non-limiting examples, respiratory rate, a relation between inspirium and expirium, oxygen saturation in room air, and lung compliance.

In some embodiments the idle period 808 optionally follows the therapeutic period 805.

In some embodiments the medication period 809 optionally follows the idle period 808.

In some embodiments the medication period 809 optionally lasts for one or more respiratory cycles; by way of non-limiting examples, three cycles, four cycles, or five cycles. Optionally, the number of respiratory cycles is less than 20. In some embodiments, the medication period 809 optionally lasts as long as useful for providing medication.

In some embodiments the medication period 809 optionally includes one or more medication cycles.

In some embodiments a device automatically applies one or more of the first sensing period 804, the therapeutic period 805, the idle period 808, and the medication period 809 to a patient, in a hospital setting, in a day clinic setting, or in a home setting.

In some embodiments a device automatically applies one or more rounds of the pulmonary therapy shown in FIG. 8 per day, per patient.

In some embodiments the device can automatically apply one or more rounds of the pulmonary therapy shown in FIG. 8 per day, for different patients. In some embodiments mouthpieces or facemasks are switched when switching therapy subjects.

Figure 9:
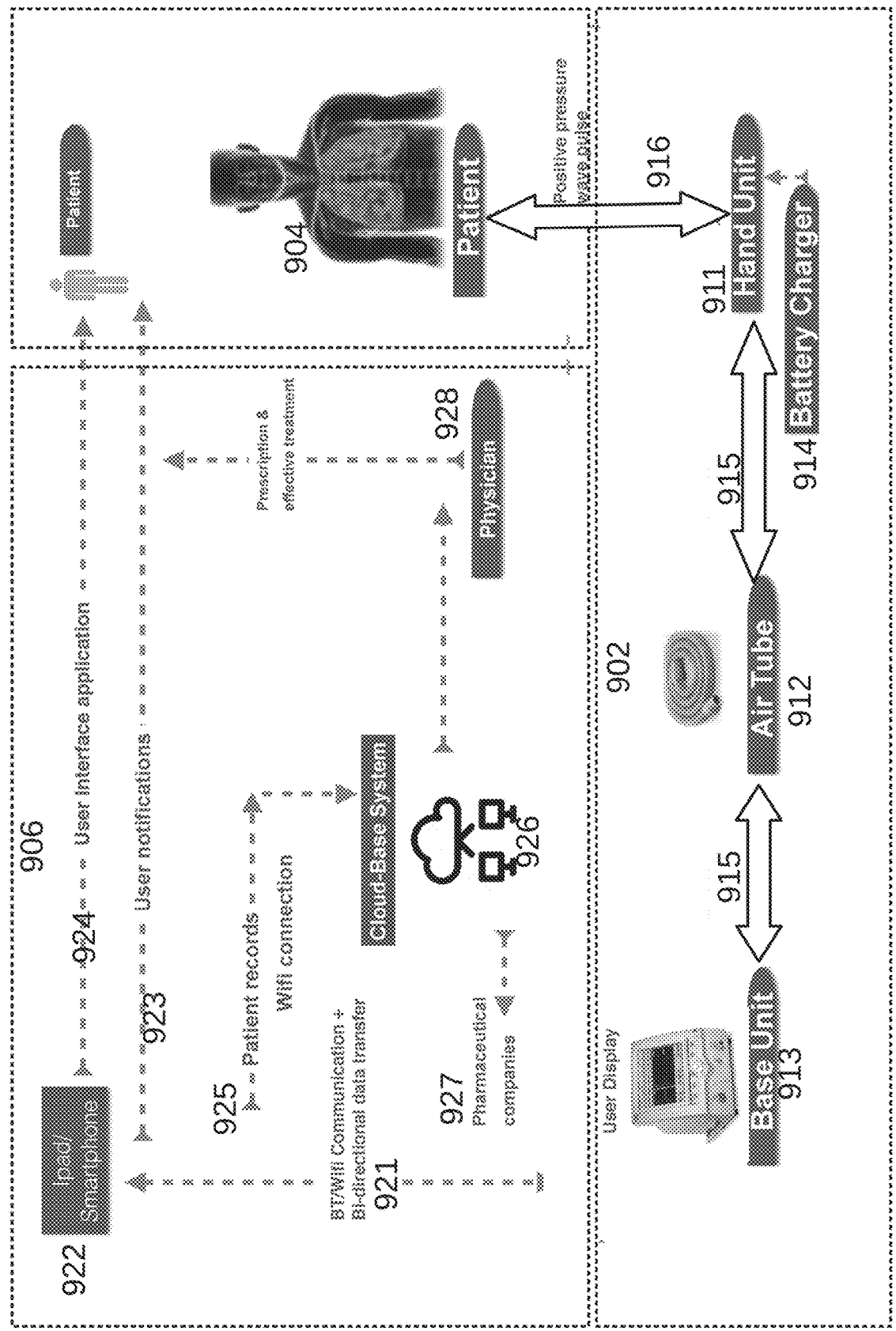
FIG. 9 is a simplified illustration of an example embodiment of a system comprising a pulmonary treatment device, according to some embodiments of the present disclosure.

Reference is now made to FIG. 9, which is a simplified illustration of an example embodiment of the invention.

FIG. 9 shows components in an example embodiment of a system 900 for collecting pulmonary data from patients and providing pulmonary physical treatment and/or pulmonary medicine. Some of the components are optional.

FIG. 9 shows a patient 904, a computing component 906 and additional pulmonary therapy components 902.

The system 900 optionally includes the computing component 906 and the additional pulmonary therapy components 902.

Some non-limiting examples of pulmonary therapy components 902 in the system 900 include:

A first unit 911, also termed a hand unit 911, optionally including a mouthpiece for placing in a patient's 904 mouth or over the patient's mouth;

A base unit 913. In some embodiments the base units provides air flow 915 via an air tube 912 or air hose 912 to the hand unit 911. In some embodiments the base unit 913 provides air flow 915 under positive pressure to the hand unit 911. In some embodiments the base unit 913 provides air flow 915 under negative pressure, that is suction, to the hand unit 911.

In some embodiments the base unit 913 includes a pulmonary sensor such as, by way of a non-limiting example, the pulmonary sensors 101 105 109 of FIGS. 1A-C.

In some embodiments the hand unit 911 includes a pulmonary sensor such as, by way of a non-limiting example, the pulmonary sensors 101 105 109 of FIGS. 1A-C.

In some embodiments the hand unit 911 optionally includes a power source, optionally a battery, optionally a rechargeable battery. In some embodiments the hand unit 911 optionally includes a power source, optionally a battery, optionally a rechargeable battery In some embodiments the hand unit 911 includes an optional adjustable valve/orifice flow resistor (not shown in FIG. 9) for optionally intermittently blocking the air flow 915, producing a positive pressure wave pulse 916 and/or a negative pressure wave pulse 916. In some embodiments the adjustable valve/orifice flow resistor optionally operates under control of a computing unit in the base unit 913 and/or built into the hand unit 911. In some embodiments the adjustable valve/orifice flow resistor optionally operates powered by an optional battery in the hand unit 911.

In some embodiments the system 900 includes a computing unit 926, optionally a cloud based computing unit 926, optionally arranged to receive data measured by one or more of the pulmonary therapy components 902, such as the hand unit 911 and/or the base unit 913. In some embodiments the cloud based computing unit 926 is optionally arranged to receive data measured by a sensor such as the pulmonary sensors 101 105 109 of FIGS. 1A-C, optionally included in one or more of the pulmonary therapy components 902.

In some embodiments the computing unit 926 optionally includes patient data 925, optionally as patient records 925.

In some embodiments a physician 928 optionally has access to data collected by the computing unit 926 and/or in the patient records 925.

In some embodiments the computing unit 926 includes a user interface 922, optionally a mobile user interface such as a tablet and/or a smartphone and/or an application which is designed to operate on a tablet and/or a smartphone.

In some embodiments a user interface (not shown in FIG. 9, yet similar to the user interface 922) is optionally provided to the patient 904, for optionally interfacing with the system 900.

In some embodiments pharmaceutical companies 927 can optionally communicate with the computing unit 926.

Various components are optionally interconnected by wired and/or wireless communications. Some non-limiting examples include:

The pulmonary therapy components 902 optionally communicating 921 with the computing component 906;

The user interface 922 of the computing component 906 optionally communicating 924 with the patient 904;

The user interface 922 of the computing component 906 optionally sending user notifications to the patient 904 and/or to a patient administering pulmonary treatment to the patient 904; and The computing unit 926 optionally communicating with the patient records 925.

The system 900 optionally includes the non-invasive, portable and handheld hand unit 911, optionally for self-use by the patient 904, optionally on a daily use, at hospital/clinic or home setting, optionally following directions of the physician 928.

Figure 10:
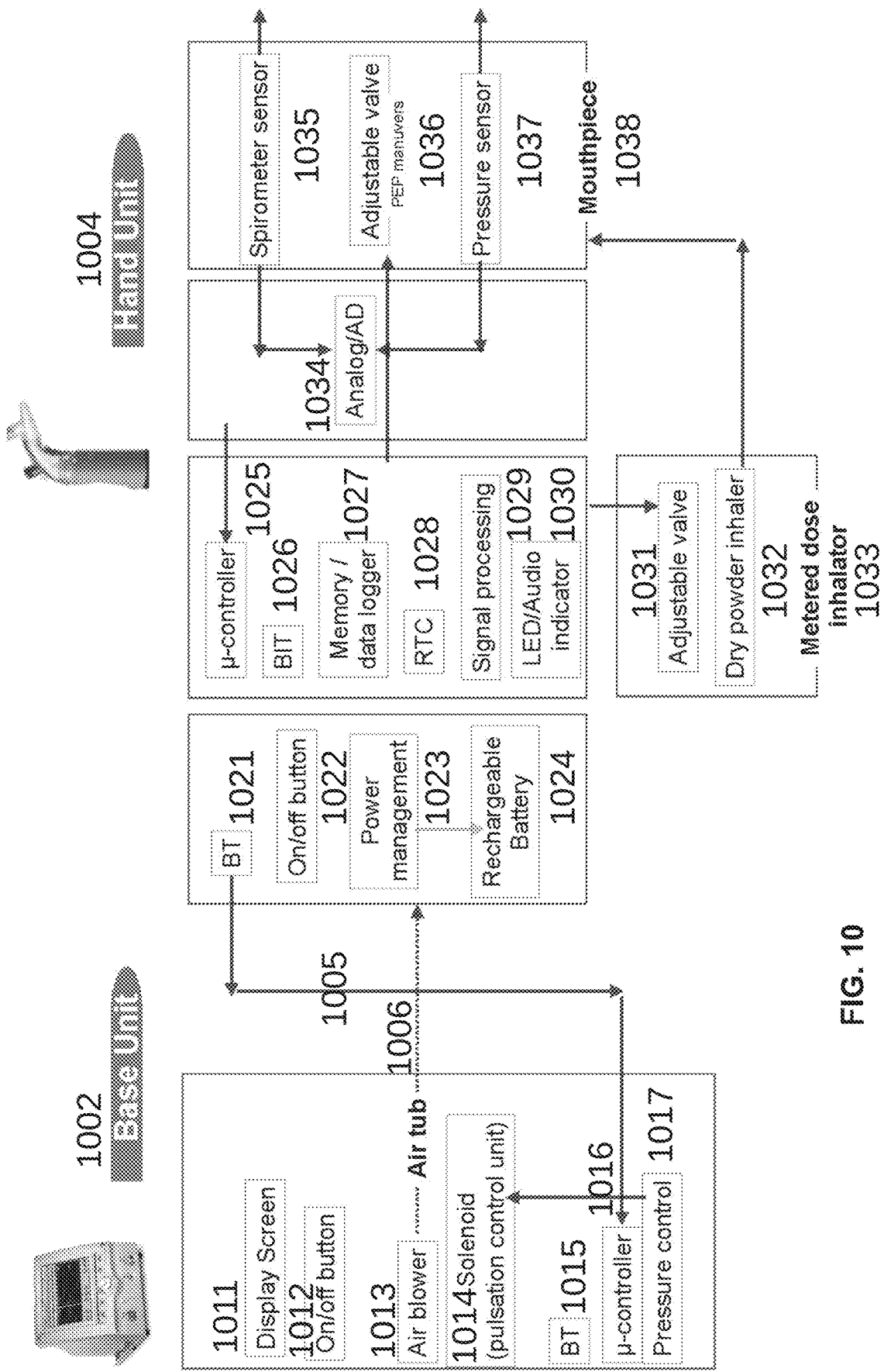
FIG. 10 is a simplified block diagram of components of a pulmonary treatment device, according to some embodiments of the present disclosure.

Reference is now made to FIG. 10, which is a simplified illustration of an example embodiment of the invention.

FIG. 10 shows some components in an example embodiment of a system 1000 for collecting pulmonary data from patients and providing pulmonary physical treatment and/or pulmonary medicine. Some of the components are optional.

FIG. 10 shows a base unit 1002 and a hand unit 1004.

The base unit 1002 and the hand unit 1004 optionally communicate 1005 with each other, optionally wirelessly communicating, optionally by Bluetooth.

The base unit 1002 optionally provides air pressure and/or air suction to the hand unit 1004, optionally by an air tube 1006.

In some embodiments the base unit 1002 optionally includes one or more of the following:

an optional display screen 1011;

an optional on/off switch 1012;

an optional air blower 1013, for providing positive pressure and/or negative pressure (suction), optionally connected 1006 to the hand unit 1004 by the air tube 1006;

an optional pulsation control unit 1014, optionally a solenoid operating an adjustable valve/orifice flow resistor;

an optional communication unit 1015, for wired and/or wireless communication, optionally a Bluetooth communication unit;

an optional micro-controller 1016 or a computing component 1016; and an optional pressure control unit 1017.

In some embodiments the hand unit 1004 optionally includes one or more of the following:

an optional communication unit 1021, for wired and/or wireless communication, optionally a Bluetooth communication unit;

an optional on/off switch 1012;

an optional display screen 1022;

an optional power management unit 1023;

an optional battery 1024, optionally a rechargeable battery 1024;

an optional micro-controller 1025 or a computing component 1025;

an optional Built-In-Test (BIT) unit 1026;

an optional memory unit 1027 and or a datalogger;

an optional Real Time Clock (RTC) unit 1028, for optionally keeping time according to a software sequence;

an optional signal processing unit 1029;

an optional warning component 1030, optionally a visible warning component 1030 such as a light, and/or an audible warning component 1030 such as a buzzer or a speaker;

an optional mouthpiece 1038, optionally including one or more of a pulmonary sensor 1035, such as a spirometer 1035; an optional adjustable valve 1036, optionally designed for performing PEP maneuvers; an optional pressure sensor 1038; and an optional dose inhalator 1033. In some embodiments the dose inhalator 1033 optionally includes one or more of a dry powder providing component 1032 and/or an aerosol producing component 1032; and an optional adjustable valve 1031, optionally designed for controlling a providing of the powder and/or aerosol.

Optionally, pulmonary sensor 1035 in the mouthpiece is augmented or replaced by another pulmonary sensor 1035; for example, an external pressure sensor and/or a statoscope.

Referring again to FIGS. 9 and 10 additional details are now provided.

The system 900 optionally includes the non-invasive, portable and handheld hand unit 911 1004, optionally for self-use by the patient 904, optionally on a daily use, at hospital/clinic or home setting, optionally following directions of the physician 928.

Hand Unit

In some embodiments the patient optionally breathes through a mouthpiece connected to an end of the hand unit.

In some embodiments the hand unit optionally includes: a mouthpiece; a housing, optionally a plastic housing; an internal airflow duct; an optional airflow adjustable shutter (optionally an adjustable shutter disc) in the airflow duct optionally at an air inlet to the airflow duct; an optional battery pack, optionally rechargeable; an optional printed circuit board PCBA (Printed Circuit Board Assembly); an optional micro-controller; an optional on/off button; an optional PEP adjustable valve; an optional air pressure sensor; and an optional spirometer sensor, optionally with a display at an expiratory/inspiratory airflow outlet.

In some embodiments the system optionally includes an algorithm with a machine learning model that personalizes and adjusts treatment parameters, such as, by way of some non-limiting examples: duration and/or pressure of pressure pulses; duration and/or order of inspiratory and expiratory patterns; timing, optionally synchronized, of intermittent mechanical ventilation provided during the therapeutic modes; and dose of aerosolized medication during the medication mode.

In some embodiments the system uses one or more of the above-mentioned sensors to collect patient data, such as lung compliance in response to medication treatment.

In some embodiments lung compliance is optionally calculated by a difference in volume divided by a pressure difference that was provided by the system.

In some embodiments an increase in lung optionally causes the system to calculate changed values for the treatments—for example shorter treatment cycles.

In some embodiments a lower respiratory rate will also optionally cause a shortening of the treatment cycles.

In some embodiments the hand unit optionally adjusts the therapeutic patterns and parameters, including dosage (comprising dose and/or dosing schedule), utilizing the algorithm. In some embodiments the hand unit automatically transmits measurement data to one or more of:

The base unit, that in some embodiments optionally adjusts the air pressure flow into the hand unit throughout the air tube;

A cloud-based server, optionally via a smartphone.

In some embodiments an algorithm, optionally stored on the base unit or the cloud-based server, analyzes the received measurements and optionally produces a statistical analysis and/or a comprehensive report, and optionally automatically sends to a patient file, optionally for further evaluation and diagnosis by a physician who can remotely review the results. The received data optionally assists the physician to diagnose patient condition, the patient response to the treatment and potentially to provide proper treatment.

In some embodiments the physician can remotely connect, for example using a smartphone, a tablet or a PC, anytime, to review measurement results and to personalize a treatment for the patient.

In some embodiments the patient can optionally receive alerts and notifications, for example to a personal computing device such as a phone or smartphone, regarding treatment or medicine compliance and/or experience, and/or instructions from his/her physician.

In some embodiments an aggregated patient data collection is a potentially useful data source for pharmaceutical companies, clinical trials and/or health insurance companies.

In some embodiments the hand unit is optionally powered by a battery, optionally a rechargeable battery, optionally using a battery charger.

In some embodiments, upon battery depletion, the patient plugs in the battery charger to recharge the batteries by connecting the battery charger to an electrical outlet or to an external charger adaptor.

In some embodiments, during battery charging, the device is optionally disconnected and not operated.

Air Tube

In some embodiments the air tube is a flexible tube allowing airflow from the base unit to the hand unit.

Base Unit

In some embodiments the base unit optionally provides a continuous positive pressure airflow source to the hand unit.

In some embodiments the base unit optionally includes one or more of: a turbine blower, optionally an off-the-shelf turbine blower; a custom PCBA (Printed Circuit Board Assembly) with control and/or pressure measurement components; an indicator or warning light, optionally a LED; an optional power switch; an optional DC input connector.

In some embodiments the base unit is optionally powered by an external power supply which plugs into a standard AC power source.

In some embodiments, while a patient is in an upright sitting and relaxed position, but not reclining, he/she holds the hand unit and breathes normally through the mouthpiece. The pulmonary treatment system introduces positive air pressure pulse(s) according to a preprogrammed protocol, optionally while receiving a continuous airflow from the base unit via the air tube connected to the hand unit, optionally through an air inlet valve.

In some embodiments the patient is typically treated by the system for short periods of time (several minutes, for example 5-30 minutes, for example 20 minutes) several times a day (for example 1-8 times per day, for example 2-4 times per day), optionally according to a physician's instructions.

Reference is now made to FIGS. 11A-11D, which are images comparing prior art treatment and treatment according to an example embodiment of the invention.

FIGs. 11A-11D show ex-vivo lungs of a pig, that was treated with an inhaled drug labeled with radioactive material. An extent of dark areas 1102 1104 1106 1108 corresponds to an extent to which the drug reached into the lungs.

Figure 11A:
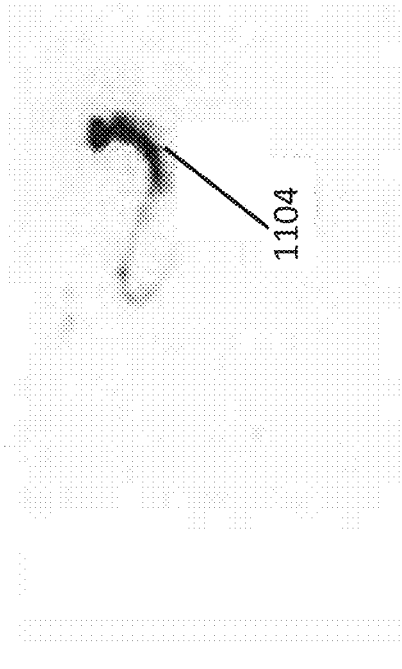
FIGS. 11A-11D are images of lungs of a pig that was treated with inhaled drug comparing a current protocol and a protocol according to some embodiments of the present disclosure.
Figure 11B:
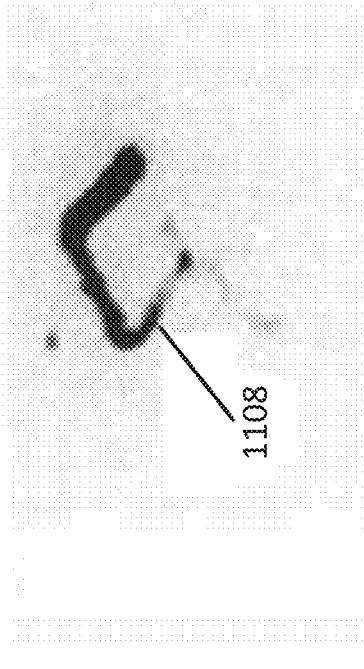

FIGS. 11A and 11B were taken after inhalation of medication in a conventional way, as is known in prior art.

Figure 11C:
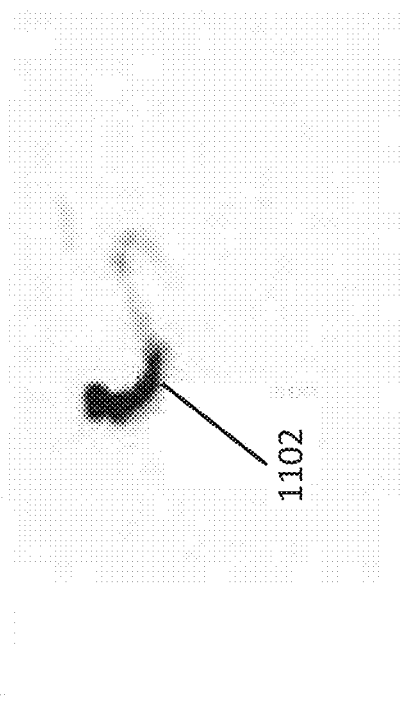
Figure 11D:
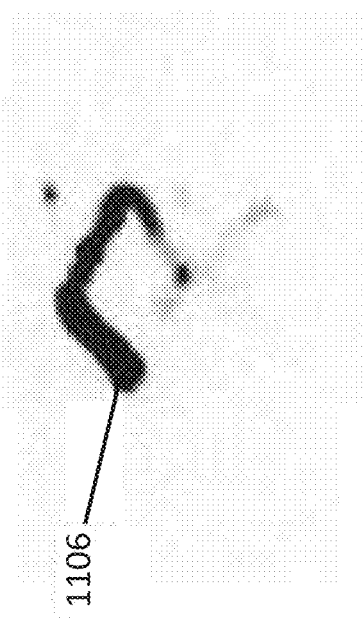

FIGS. 11C and 11D were taken after physical treatment and inhalation of medication according to an example embodiment of the invention.

It is shown that according to the prior art the medication is mainly located in the trachea whereas according to an example embodiment of the invention the drug penetrated deeper, reaching to the bronchi.

Figure 12:
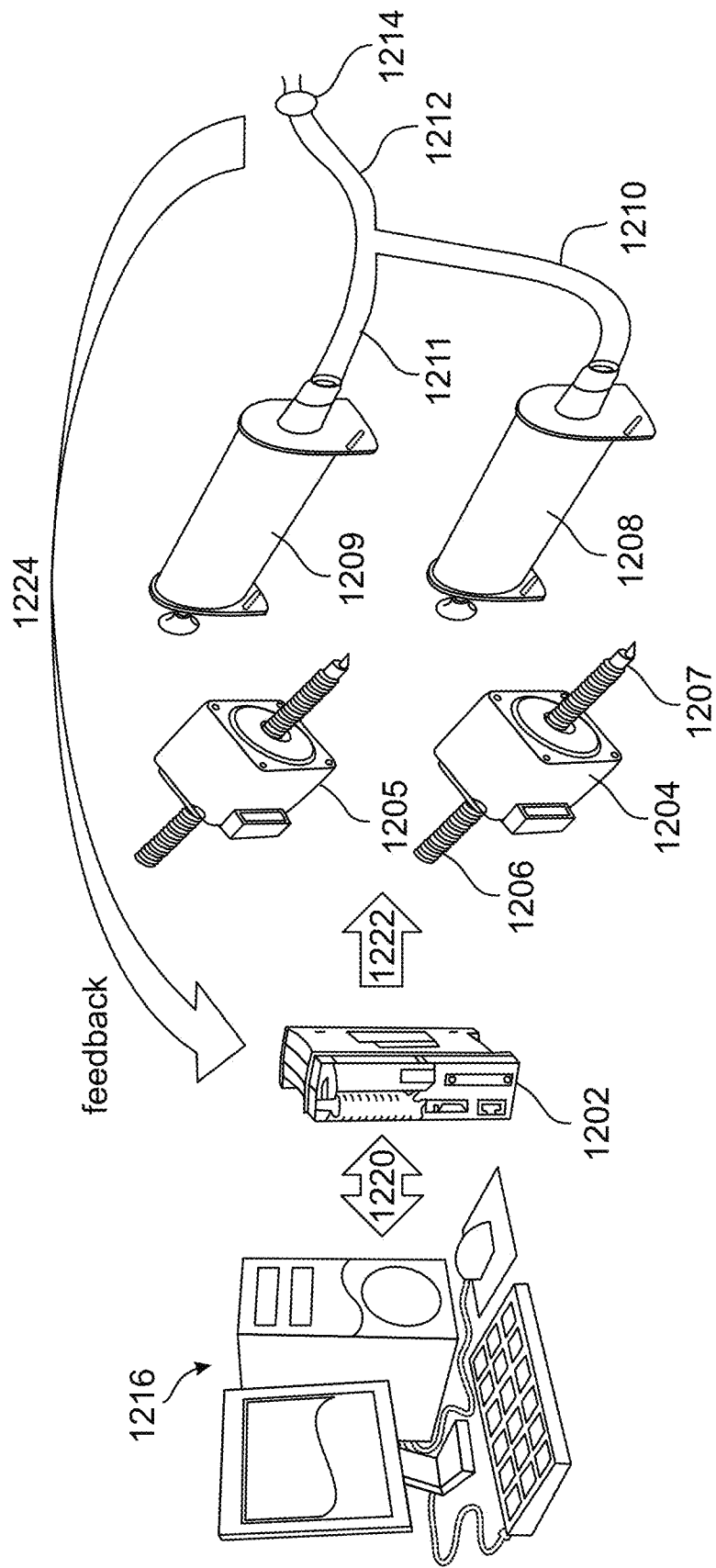
FIG. 12 is a simplified illustration of a pulmonary medicine administering subsystem, according to some embodiments of the present disclosure.

Reference is now made to FIG. 12, which is a simplified illustration of an example embodiment of the invention.

FIG. 12 shows some components in an example embodiment of a system for providing pulmonary treatment to patients. Some of the components are optional.

FIG. 12 shows:
- an optional control computer 1216, optionally communicating 1220 with an electronics unit 1202;
- the electronics unit 1202 optionally providing control commands 1222 to one or more motors 1204 1205, optionally powering 1206 1207 one or more air pumps 1208 1209, connected by one or more hoses 1210 1211 to a facemask (not shown).

In some embodiments the one or more hoses 1210 1211 are optionally connected to one hose 1212 before being connected to a facemask (not shown).

In some embodiments an optional expiration valve 1214 is included in the one or more hoses 1210 1211, in the one hose 1212, or in the facemask.

In some embodiments the optional control computer 1216 is optionally packaged together with the electronics unit 1202.

Ventilator Breath Cycle Protocols and Composite Protocols

Figure 13A:
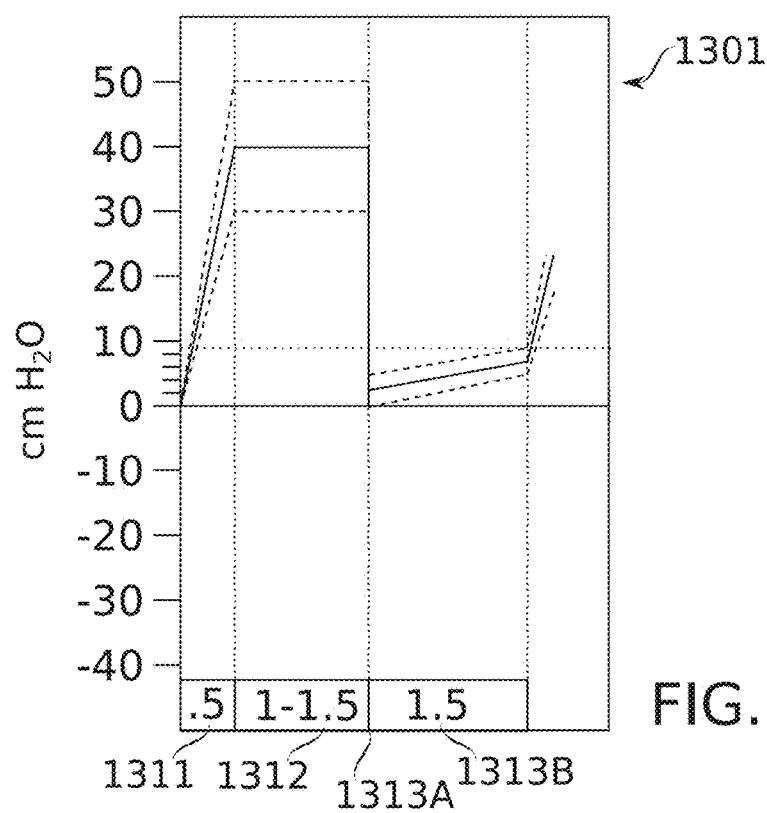
Figure 13B:
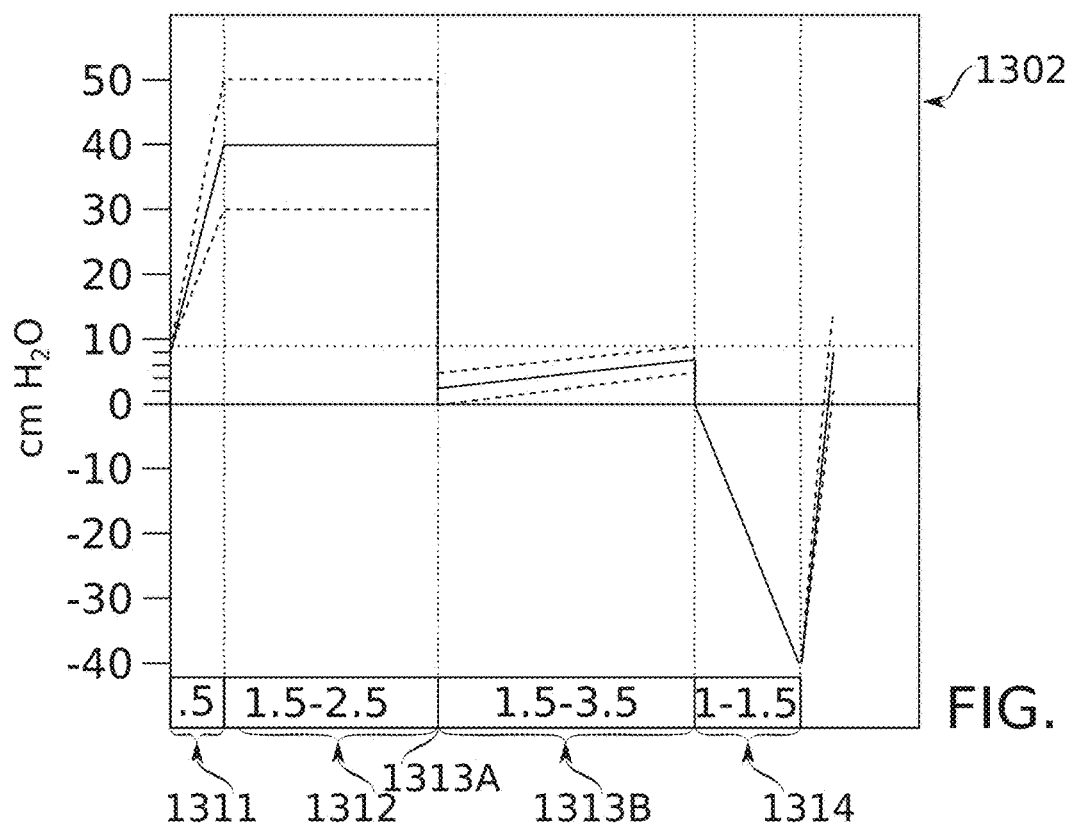

Reference is now made to FIGS. 13A-13C, which are charts schematically representing ventilator breath cycle protocols 1301, 1302, 1303 configured to produce recruitment effects within the lungs, according to some embodiments of the present disclosure. Reference is also made to FIG. 14, which schematically represents a sequence of ventilator breath cycle protocols 1301, 1302, 1303, according to some embodiments of the present disclosure.

Herein, a "ventilator breath cycle" refers to a full cycle between the beginning of a first inspiration and the beginning of the next inspiration, the timing and pressures of which is substantially under mechanical control. The mechanical control is optionally asserted by a system which is an invasive ventilator (e.g., intubating ventilator), non-invasive ventilator (e.g., mask ventilator), or another respiratory therapy device capable of establishing an appropriate range of lung pressures needed for administering the protocol (e.g., a cough assistance and/or medication delivery device). In some embodiments, the respiratory therapy device is a device which is used continuously for assisting ongoing breathing; but configured to intermittently administer, e.g., one or more of the protocols of FIGS. 13A-13C and/or 14. In some embodiments, the respiratory therapy device is used for administering respiratory therapy during separated epochs. Epoch durations may be, for example, between about 30 seconds and 10 minutes. The epochs may be separated, for example, by periods of about 2 hours, 4 hours, 6 hours, 8 hours, or another period. Optionally, the epochs are spaced more closely in time, e.g., occurring every few minutes.

Parameters of Breath Cycle Protocols

As will be discussed after detailing the parameters of each protocol, breath cycle protocol 1301 is a conditioning protocol, intended primarily for re-recruitment (to a more functional role in gas exchange) of de-recruited lung regions without aspiration of mucous. Breath cycle protocols 1302, 1303 continue to perform substantially the conditioning of breath cycle protocol 1301 (targeted at larger airways and smaller airways, respectively) with the addition of aspiration of mucous during a segment of expirium.

More specifically:

At period 1311, each of breath cycle protocols 1301, 1302, 1303 begins with an "inspirium rump" of about 0.5 seconds, which inflates the lungs to a positive pressure within a range of about 30-50 cm $H_2O$. Herein, references to pressure values in centimeters of water refer to pressures above (positive value) or below (negative value) ambient atmospheric pressure. Positive pressure represent inflation of the lungs; negative pressure represent suction applied to the lungs.

The positive pressure actually used is preferably selected according to the state of the individual patient. It should be low enough to avoid damage due to overpressure, but still high enough to induce flow along high-resistance (e.g., collateral) airways. The inflation pressure may be somewhat higher than would be permissible for a chronically maintained ventilation protocol, since it is to be administered for just a few breath cycles each time.

During period 1312, there is an inspirium hold. The inspirium hold is optionally of different durations, which said different durations may respectively target different airway sizes (or lung "depths") for re-recruitment. Differences among airways of different sizes/depths which are potentially relevant to hold-length targeting are further explained hereinbelow. Of the examples shown:

- Protocol 1301 has an inspirium hold of a duration selected from within a range of about 1-1.5 seconds, and targets small airways.
- Protocol 1302 has an inspirium hold of a duration selected from within a range of about 1.5-2.5 seconds, and targets large airways.
- Protocol 1303 has an inspirium hold of a duration selected from within a range of about 0.8-1.5 seconds, and targets small airways.

The ranges given are examples. They demonstrate differences in inspirium hold times which may differentially target different regions of a lung. In some embodiments, the duration of the inspirium hold in any of the protocols 1301, 1302, 1303 is within a range of about 0.5 seconds to about 5 seconds. Herein, "inspirium" is also referred to equivalently as an "inhalation phase", or an "inspiratory phase"; and "expirium" is also referred to equivalently as an "exhalation phase" or "exhale phase". As a baseline definition, times of maximum and minimum lung volume mark the boundaries between these phases. However, when respiratory pressures are mechanically manipulated, the definition becomes somewhat a matter of which conventions are adopted. Herein, at least as the terms apply to the protocols, e.g., of FIGS. 13A-13C, the inspiration phase begins with the inspirium rump, upon initiation of a substantially monotonic rise from a lung pressure at or below about 10 cm $H_2O$ of atmospheric pressure to a high positive lung pressure (e.g., of about 30-50 cm $H_2O$). It ends (and expirium or "exhalation phase" begins) after peak lung volume is achieved, and with the beginning of a substantially monotonic decline in lung pressure towards a value that remains at or below about 10 cm $H_2O$ of atmospheric pressure (optionally, below about 9 cm $H_2O$) until the onset of the next inhalation phase. This period of lowered lung pressure also includes the time of minimum lung volume of the breath cycle. Oscillations in pressure which result in lung volume fluctuations of less than about 10% of the total change in lung volume over the course of the breath cycle do not prevent an otherwise monotonic rise/fall in pressure from being considered "substantially" monotonic.

The period of expirium in each breath cycle protocol initiates with a drop in ventilator pressure to at or near 0 cm $H_2O$ (at time 1313A). In some embodiments, the ventilator pressure drops to a selected value within a range between about −5 cm $H_2O$ and about 5 cm $H_2O$. In some embodiments, the ventilator pressure drops to a value at or above 0 cm $H_2O$, and below 5 cm $H_2O$. The drop at time 1313A is shown as effectively instantaneous; however, it will physically occur over a somewhat longer time; e.g., since the system remains out of equilibrium during this period due to changing lung volume. Change in lung volume tracking the drop in ventilator pressure is, of course, not instantaneous, so pressure in the lung may remain elevated for a period following the change in ventilator pressure.

Time 1313A is followed by a period 1313B of gradually elevating positive expiratory pressure (PEP), e.g., up to a pressure within a range between about 5-9 cm $H_2O$ over a period selected from within a range of about 1.5-3.5 seconds. The drop at 1313A is also referred to herein as an "undershoot", relative to pressure during period 1313B. Optionally, the peak (e.g., end) PEP is in a range of about 3-10 cm $H_2O$; or, in some embodiments, in a preferred range of about 5-9 cm $H_2O$. In some embodiments, the lung volume of the patient reaches a minimum during a period of PEP wherein the pressure is larger than the lowest pressure exerted during the expiration phase of the breath cycle.

Potential effects of this ramping up of PEP over time after an initial drop are further discussed hereinbelow.

In protocol 1301, period 1313B is preferably selected from the short end of that range (e.g., 1.5 seconds).

In protocol 1302, 1303, period 1313B may be longer, which potentially assists in stabilizing re-recruitment (e.g., as discussed hereinbelow) before the administration of suction during period 1314. During period 1314 (present only in protocols 1302, 1303), suction is applied. In some embodiments (e.g., as illustrated), suction comprises decreasing pressure down to about −40 cm $H_2O$ over a period of about 1-1.5 seconds, after which pressure begins to ramp up again as a new breath cycle begins. Suction potentially helps mobilize mucous upward and/or out of the lungs. Optionally, the suction pressure is another pressure, chosen, e.g., from within a range of about −20 to −40 cm $H_2O$.

It should be understood that the ramp up in pressure during periods 1311, 1313B and the ramp down during period 1314 are not necessarily straight lines. There may be delays in pressure changing (particularly during periods 1311, 1314) due in part due to the interaction of ventilator-generated pressure with the relatively large lung volume changes which occur during this time. In the case of the relatively small pressure changes occurring during period 1313B, a relatively reduced need for airflow may result in less lag between ventilator-generated pressure and lung volume changes.

It is noted that in some embodiments, an existing ventilator and/or other respiratory assistance system (e.g., a cough assistance system) is reprogrammed to provide pressure according to the breath cycle protocols of FIGS. 13A-13C. In some embodiments, medicine is given in conjunction with a sequence of mechanically assisted lung portion recruiting and/or expectoration breath cycles; for example, using a pulmonary therapy protocol as described in relation to FIGS. 7A-7B.

Concatenations of Breath Cycle Protocols

FIG. 14 illustrates an optional order in which the breath cycle protocols 1301, 1302, 1303 may be concatenated. The protocol of FIG. 14 may be appropriate, for example, for use with a patient with presenting with most or all of a high heart rate, high respiratory rate, low respired volume, high lung resistance, low lung compliance, copious viscous secretions, fatigue, and asymmetrical breathing. In some embodiments, the protocol of FIG. 14 or another protocol incorporating the breath cycles of FIGS. 13A-13C is provided to a patient in order to promote $CO_2$ exchange.

In some embodiments, only one of the last two breath cycle protocols 1302, 1303 is used. For example, omitting breath cycle protocol 1303 may be appropriate for a patient presenting with elevated lung resistance, low chest resistance, poor lung compliance, and copious discharge, but lacking in the other signs just mentioned.

Each breath cycle protocol which is used occurs one or more times, to a total count indicated by the brackets subscripted with $n_1$, $n_2$, and $n_3$, where the subscripts are integers, optionally in the range of 1-10, and preferably within a range of 1-3. For example, there are optionally 3 applications of breath cycle protocol 1301, followed by 2 applications of breath cycle protocol 1302, and again 3 of breath cycle protocol 1303.

These numbers ($n_1$, $n_2$, and $n_3$) represent protocol cycle counts in a concatenated series of breath cycle protocols which is not interrupted.

Optionally, in any of the breath cycle protocols (including concatenations thereof), there is a provision for suspending or aborting the protocol upon interruption by respiratory movements initiated by the patient, e.g., cough. Coughing is potentially elicited by the protocol sequence itself, and may itself serve to aid lung clearance and/or re-recruitment. In some embodiments, cough detection is based on pressure sensing; e.g., sensing of an onset of negative pressure due to patient-initiated inspiration.

The protocol (and the sequence of protocols of which it is a part) is optionally suspended during the cough, and restarted again after the cough is completed. Optionally the protocol sequence restarts exactly at the interrupted breath cycle protocol. Optionally (e.g., when interruption occurred during a breath cycle protocol 1302, 1303 comprising a suction period 1314 that was interrupted), the lung is reconditioned upon resumption by one or more (e.g., 1, 2 or 3) cycles of a conditioning protocol 1301, before continuing with the cycle in which a period of suction is administered.

In some embodiments, a first breath cycle protocol in a sequence is triggered to begin in synchrony with an existing respiratory rate of the patient; e.g., to begin after patient-controlled expirium. The sequence is optionally administered at intervals, e.g., of several minutes or hours (for example, every 10-60 minutes, every 4 hours, every 8 hours, or every 12 hours). In some embodiments, a cough by a patient initiates a protocol sequence, for example, the sequence of FIG. 14. In some embodiments, a spontaneous cough itself elicits a version of the sequence of FIG. 14, e.g., 1-3 cycles of protocol 1301, followed by 1-3 cycles of protocols 1302 and/or 1303.

It is noted that in some embodiments, an existing ventilator system is reprogrammed to provide pressure according to concatenations of breath cycle protocols, optionally interrupted upon cough sensing; for example as just described in relation to FIG. 14.

Potential Physiological Effects of Breath Cycle Protocols

In some respiratory disease states, significant portions of the lungs become de-recruited, so that they no longer play as effective a role in the respiratory exchange of gasses. Other portions remain recruited, and some of these portions may even be at about the same depth (distal position) within the lung as the portions that have been de-recruited. A concern in ventilation of such patients is to re-recruit de-recruited portions if possible. Two potential mechanisms of this include removal of mucous which restricts (e.g., plugs) air access to de-recruited areas, and reinflation of collapsed lung structures. Ventilator-based treatments to induce re-recruitment potentially exist in a tension between these two mechanisms. Suction to remove mucous (and reduce plugging) could tend to induce lung tissue collapse. Conversely, positive pressure to induce lung inflation (and increase available surface area for gas exchange) could send mucous more distally. However, there is also a way by which positive pressure can be exploited to move mucous proximally, which may be exploited to potentially reduce some of the conflict between the two mechanisms. Within the same and/or different breaths, features may by introduced to the expiration phase which allow suction to be introduced while minimizing interference with positive-pressure generated mechanisms of re-recruitment.

While the descriptions of this section are made with particular reference to the breath cycle protocols of FIGS. 13A-13C, it should be understood that concepts outlined also apply, changed as necessary for the specifics of the protocol, to protocols described in relation, e.g., to FIGS. 4, 5, 7A-7B, and/or 8.

Re-Recruitment Using Collateral Airways

In relation to FIGS. 3A-3B, there are described herein alternate sets of airways for filling of lung tissue; "direct" airways arranged in a generally proximal to distal direction through the main branching structure of the lung, and collateral or "indirect" airways existing within individual levels of that branching structure, and/or crossing between different levels among branches already divided by a more proximal branch point. Examples of such collaterals include interbronchiolar channels of Martin, bronchiole-alveolar channels of Lambert, and/or interalveolar pores of Kohn. Without commitment to a particular physiological theory, these collateral airways may play a role in resolving the aforementioned tension, in some embodiments of the present disclosure.

In any given region of the lung, the two classes of airway (main branches and collaterals) may have different normal resistances to the passage of air, and moreover be differentially subject to occlusion. In particular, healthy collateral airways may have relatively higher resistance compared to healthy "direct" airways at the same structural level of the lung. In a disease state, however, the direct pathways may plug (with mucous) and/or collapse in regions of the lung to which patent collateral airways nevertheless persist. For this or another reason (the full dynamics of lung function remain to be elucidated), slow filling via collateral pathways may be possible in lung regions which have become relatively inaccessible via normally faster-filling direct pathways.

Lengthening the high positive pressure phase of inhalation potentially takes advantage of this (corresponding, in some embodiments, to period 1311 of a breath cycle protocol). In a first instance, this may allow recruiting more lung surface area for gas exchange; and potentially, in a second instance, even re-opening of some collapsed spaces (e.g., collapsed alveoli). There is potentially opening of the collateral airways themselves, e.g., opening of the interalveolar pores. The choice of positive pressure value during the inspirium hold (e.g., from a range between 30-50 cm $H_2O$) is optionally adjusted according to the compliance of the patient lung; e.g., selected to be low enough to avoid damage to overpressure, but still high enough to induce flow along high-resistance (e.g., collateral) airways. For lungs with small remaining capacity and/or lungs of children, pressures and/or extended positive inspiration pressure periods are optionally reduced, e.g., by about 25%, 33%, or another value. In patients with flow restrictions, the inspiration pressure period is optionally increased, e.g., by about 25%, 33%, or another value. Other considerations optionally affecting selection of the duration of the positive pressure phase are discussed hereinbelow.

Collaterally-filled lung regions may go on to experience relatively increased pressure during expiration compared to directly filled lung regions. This is insofar as the collateral pathways that slowly filled these regions retain enough resistance that they also release pressure relatively slowly. Relatively rapid release, suction, and/or compression of the lung to initiate exhalation may then induce pressure gradients that contribute to dislodging obstructive material (e.g., mucous) in a proximal direction along airways of the main branching structure of the lungs.

Supporting Re-Recruitment of Collaterally Pressurized Lung Regions

There is a potential issue of how preferably to support the use of elevated distal pressure (e.g., developed with the assistance of collateral airways) to move mucous proximally. In some embodiments, a period of negative pressure (suction) may be used to assist, from a proximal side, in the proximal movement of obstructive material. A concern this approach raises, however, is how to manage the risk of de-recruitment of lung regions as inhalation pressure is removed. In some embodiments of the present disclosure, de-recruitment is managed (e.g., prevented, diminished, and/or maintained in an acceptable balance with recruitment) by a protocol which divides the expiration phase of a breath into segments. This potentially allows at least some of the desired effects of both collateral pressurization and direct suction to be obtained, by managing their tendency to mutually interfere.

Pre-Suction Expiration

There is potentially a difference in the expiratory effects on the lung of (1) negative air pressure (suction) compared to (2) squeezing by elastic body wall pressure. For example: proximal to (upward from) the location of a single blockage, airways are exposed, during applied suction, to an elevated chance of airway shrinkage, and perhaps closure-since surrounding tissue pressure remains the same. This shrinkage and/or closure can interfere with the movement of deep mucous by shifting the pressure gradient upward in the airway, away from where it could act across more distal blockages to loosen them. A more distal "recruited" area could potentially even become de-recruited due to restricted air access through a branch location more proximal that collapses.

Conversely, squeezing during expiration from elastic body wall pressure avoids exerting negative pressures, and can also act to sharpen pressure gradients across distal blockages. However, the maximum pressure differential available is generally less than suction can provide.

In some embodiments of the present disclosure, the phase of the ventilation protocol is segmented. In a first, optionally very brief segment (e.g., corresponding to time 1313A of any of FIGS. 13A-13C), ventilator pressure is reduced to an undershoot pressure. The term "undershoot" indicates reduction by a relatively large step to a lower pressure relative to pressure beforehand, which is then raised (more gradually, and by a smaller step) during later period 1313B. The undershoot pressure may be zero or close to zero (e.g., to up to a positive pressure of about 5 cm $H_2O$). This allows the lungs to subsequently deflate, without inducing potentially constricting or collapsing effects due to suction. During this period, the effects of elastic body wall pressure may additionally act to assist exhalation. It is a potential advantage to quickly drop the pressure as far as possible without exerting suction (i.e., to zero pressure) to maximize pressure differentials that may assist expectoration, while avoiding a risk of suction-induced collapse. Optionally, a small amount of suction (e.g., up to about −5 cm $H_2O$) is applied as the undershoot pressure, but quickly reversed in a second segment of the expiratory phase next described. The reversal preferably is quick enough to occur before the lungs reach their minimum volume for the breath cycle. This potentially prevents the undershoot pressure from inducing collapse of small airways. A period of steepest pressure gradients and/or highest small airway velocity immediately following time 1313A is potentially the period when the most movement of mucous is obtained. Once this period passes, moderating the undershoot pressure to a PEP potentially has a diminished impact on the effectiveness of recruitment and/or mucous movement.

In the second segment of the expiratory phase (corresponding, in some embodiments, to period 1313B of FIGS. 13A-13C), expiratory pressure is increased again to generate PEP. In some embodiments, this increase is provided as a ramp-up over a period of time, e.g., to a pressure between about 5-9 cm $H_2O$ (e.g., 8 cm $H_2O$) over a time of about 1.5-3.5 seconds. This potentially acts as a buffer against de-recruitment (e.g., by collapse), but since it phases in late, it has a lessened effect on pressure-generated movements of mucous during the immediate onset of exhalation.

More particularly, it has been reported that a positive end-expiratory pressure (PEEP, which may be considered as PEP which exists at the end of the expiratory phase) may assist in avoiding de-recruitment of lung regions (e.g., de-recruitment due to collapse when sustaining internal pressure abates). In some embodiments of the present disclosure, a drop to about zero exerted pressure in the earliest segment of the expiratory phase nonetheless may potentially avoid this collapse, since the lungs themselves are still full of sustaining air being mobilized by pressure differentials and/or the elastic recoil of the body wall. Then, as pressures approach equilibrium and/or elastic recoil nears its end, ramping up PEP dynamically is performed, in some embodiments. This provides a supporting PEP in time to potentially prevent collapse, but substantially after the period of greatest pressure gradient generation.

It is emphasized that the period of inspirium hold need not be very long. The inspirium hold may be for example, within a range of about 0.5 seconds to 5 seconds. Inspirium holds in the example protocols of FIGS. 13A-13C range from about 0.8 seconds to 2.5 seconds. Such hold durations do not necessarily result in complete back-pressurization along collaterals (i.e., a longer hold may result in more air filling than the hold durations indicated will achieve, at least initially). However, a sequence of cycles comprising brief holds potentially has cumulative effects: e.g., due to re-recruitment of other regions that provide new airways, and/or by lowering resistance within the collaterals themselves. While a very long inspirium (e.g., up to 20, 30, or more seconds) is not ruled out, it is a potential advantage to administer a breath cycle protocol which maintains an approximately normal breathing rate, e.g., of a breath at least about every ten seconds. This may be more comfortable for the patient (e.g., allowing administration more often), and may also be safer, e.g., by avoiding extended period of high lung pressurization. It may also be possible to safely select a higher inspirium hold pressure for a patient (e.g., closer to 50 cm $H_2O$) when using a shorter inspirium hold time. This may help increase peak pressure gradients available for use in re-recruitment, while reducing tissue damage that long inspirium hold times may exacerbate.

Significant attention is paid, in these protocols, to management (e.g., optimization) of the effects of back-pressurization, insofar as it does occur. This comprises (1) giving the back-pressurization at least a few moments with a steep pressure gradient to push across, (2) moderating that steep gradient so that it does not itself cause de-recruitment effects. In particular, in some embodiments: upon the initiation of expiration, pressure gradients across blockages are generated which are steep-since maximum PEP is postponed. However, they are limited not to be too steep: first because they are generated using expirium pressures close to atmospheric pressure and using body wall elasticity; and second, because a PEP is eventually introduced to prevent collapse-type de-recruitment. It is noted again that gains in recruitment on earlier breath cycles-even if small—may be built upon by subsequent breath cycles, resulting in a larger total effect.

It is noted, for the sake of clarification, that a lower-then-higher pattern of PEP (e.g., ramping up from between 0-5 cm $H_2O$ to between 5-9 cm $H_2O$) may allow a greater initial volume decrease in the lungs, which reduces in magnitude as the PEP ramps up. Whether this happens depends on factors which may be specific to the patient condition and/or the specific protocol parameters chosen. In such cases, the "PEP" ramp could actually generate slight inhalation. However, by a convention adopted herein the ramp is still referred to herein as comprising positive expiratory pressure, with inhalation proper beginning with the rapid rise toward a high inhalatory pressure of e.g., about 30-50 cm $H_2O$.

The PEP is optionally followed immediately by the beginning of the next inhalation phase (making it also a PEEP); as described, for example, in relation to FIG. 13A. These are also referred to herein as "conditioning" cycles. These cycles have the potential advantage of re-recruiting new lung portions without allowing them to experience any period of lowered pressure which might tend to generate de-recruitment.

Suction-Assisted Expiration

Conditioning cycles may not generate a desired amount of expectoration.

Accordingly, in some embodiments, some respiratory cycles may alternatively conclude with a third, suction segment (corresponding, in some embodiments, to period 1314 of FIGS. 13B-13C). Insofar as potential advantages of collateral pressurization have already been obtained for the cycle (and optionally for previous cycles), the use of suction at this point will potentially be less disadvantageous to mobilization of mucous by this mechanism.

There may still be some danger of suction-induced collapse. Previous conditioning potentially puts the lung in a state where whatever collapse does occur still leaves behind a net improvement in recruitment in place, considered over the whole sequence of cycles. The balance of conditioning cycles and suction cycles is optionally adjusted to help ensure this net improvement. From this perspective, a portion of the recruitment gains during conditioning may be seen as sacrificial, for the benefit of allowing mucous extraction to occur without creating unsustainable impairment to recruitment.

Nevertheless, earlier proximal movement of mucous may itself in part mitigate collapse (and de-recruitment) effects. Proximal movement of mucous during the first two expiratory segments potentially even places it where it can help "catch" the pressure gradient exerted in the third expiratory segment, partially protecting regions of the lung distal to it which may themselves have just been cleared.

From another perspective, some initially more distal mucous may undergo two phases of movement: a first phase of being "blown" upward (proximally) from collateral-pressurized distal lung regions (optionally with an elastic body wall assist), and then a second phase of being "sucked" upward (further proximally) by negative ventilator pressure. It may be noted that this is in part a potential method of moving mucous at different depths within the lung at different times within the breath cycle protocol itself.

Exploiting Differential Collateral Filling Times

Another way of potentially focusing expectorant effects of a ventilator protocol to more distal or more proximal levels of the lung is to adjust the duration of the inhalation hold. Different collateral ventilation pathways and their interconnected compartments may result in different filling times at different distal levels of the lung.

For example, it is noted that more proximal (upper-level) collaterals will tend to be longer than more distal (deeper-level) collaterals, and furthermore will have larger volumes to fill. Channel/pore diameter differences may at least partially counteract this difference. The difference may not be the same among all patients; e.g, elevated viscous resistance among interalveolar pores may slow pressure transfer among interconnected alveoli.

In some embodiments, a ventilation protocol uses different inhalation hold times for different inhalation cycles. Potentially, this allows addressing blockages at different lung levels. For example, in some embodiments, a patient with a slower-filling more proximal lung region and a faster-filling more distal lung region is treated with one or more ventilator cycles having a relatively prolonged inhalation hold, followed by one or more ventilator cycles having a relatively shorter inhalation hold.

The long hold, in this example, tends to move the pressure gradient proximally ("upward") in the lung. Upon lowering expiratory pressure to zero, for example, more proximal blockages will have almost the full pressure difference exerted across them, while many blockages more distal will be shielded from the pressure difference due to collateral filling that has completed above them.

Optionally, e.g., after at least one long hold cycle (e.g., 1-5 long hold cycles), a shorter hold cycle may be introduced. Upon initiation of exhalation, more proximal lung regions limited to collateral filling will potentially not yet be as fully pressurized, as more distal lung regions. The pressure gradient moves deeper, correspondingly. Optionally, groups of long- and short-hold respiratory cycles are alternated, as new recruitment at either relative level (more proximal or more distal) may affect the potential for recruitment at the other level.

Remarks on Breath Cycle Protocols of Other Figures

Within the framework just outlined, the therapeutic protocol of FIG. 4 may be understood as an example of a "conditioning" protocol which lacks, in comparison to protocol 1301, the period of pressure undershoot and ramp-up to an end pressure near the end of the exhalation phase. Instead, the end pressure is set to begin exhalation, and maintained thereafter. While this may give up some benefit of a larger initial pressure gradient strength, it also provides a non-suction but relatively high-gradient pressure step, buffered by a positive end-expiratory pressure (PEEP).

The therapeutic protocol of FIG. 5 may be understood as a "suction" breath cycle protocol like protocols 1302, 1303; but having a shortened period of end pressure (also without a pressure undershoot and ramp) with the exhalation phase also ending with a period of suction.

Examples of Lung Clearing

Reference is now made to FIGS. 15A-15D, which show imaging results of a living pig experimental subject before (FIGS. 15A-15B) and after (FIGS. 15C-15D) administration of a protocol to re-recruit lung regions de-recruited by injection of CF patient sputum, according to some embodiments of the present disclosure.

FIGS. 15A-15B show CT-imaged cross-sections of pig lung at different levels, before protocol administration. Light area 1501 comprise infiltrates to the lung (the injected sputum). Before treatment, it was estimated that the right lung had a relative share of total ventilation of about 28.95%, and the left lung a relative share of about 71.05%.

Figure 15C:
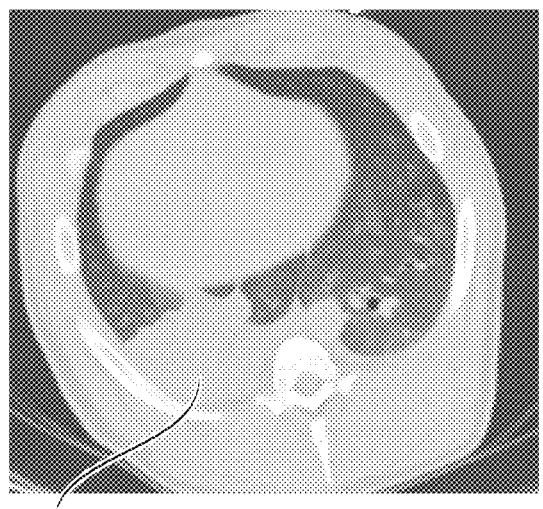
Figure 15C:
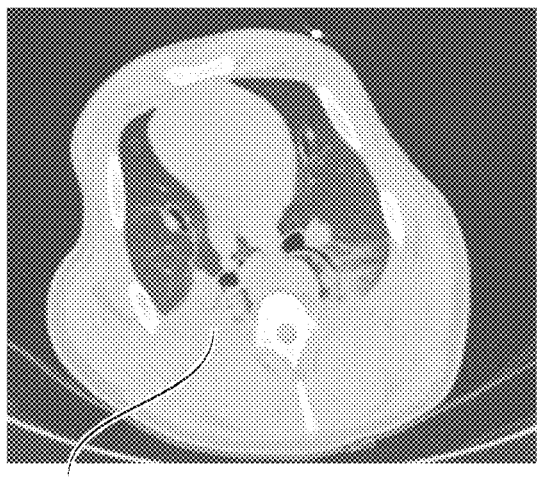
Figure 15C:
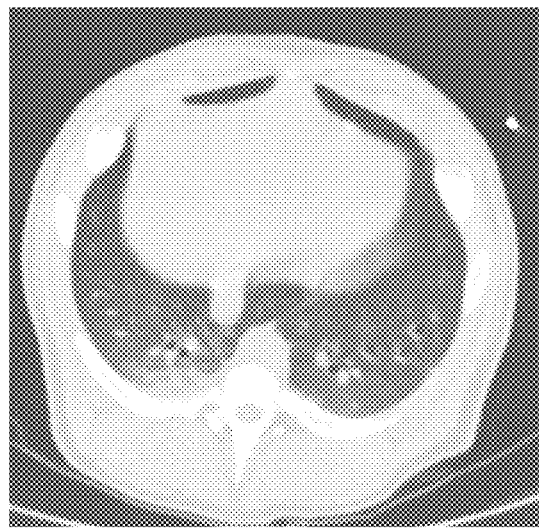

FIGS. 15C-15C show imaged cross-sections of the same pig lung and levels, after protocol administration. The protocol comprised combinations of collateral inflation and suction, for example as described in relation to FIGS. 13A-13C.

Infiltration is reduced, and lung areas are more equalized. After treatment, it was estimated that the right lung had a relative share of total ventilation of about 51.2%, and the left lung a relative share of about 48.75%. This suggests very complete cleaning was accomplished.

The inventors have also found equalization of physiological lung capacity gaps in unprepared pig lung, e.g., from right lung/left lung ventilation shares of 54.85%/45.15% to shares of 52.05%/47.95%.

Figure 15D:
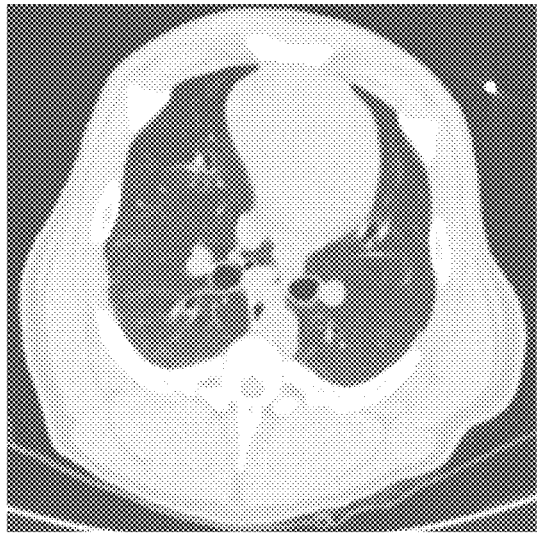
Figure 16A:
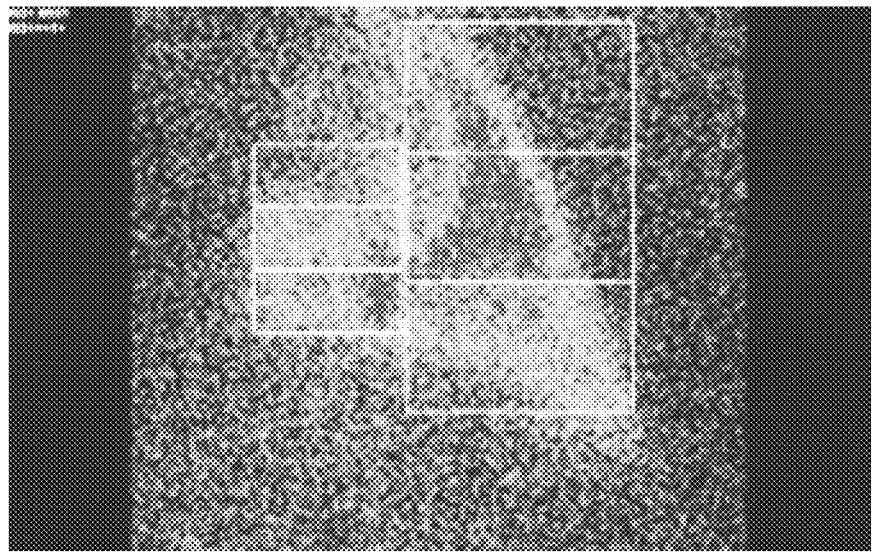
FIGS. 16A-16B schematically represent deposition of radiolabeled diethylenetriaminepentaacetic acid (DPTA) particles, in the pig lung of FIGS. 15A-15D, according to some embodiments of the present disclosure.
Figure 16B:
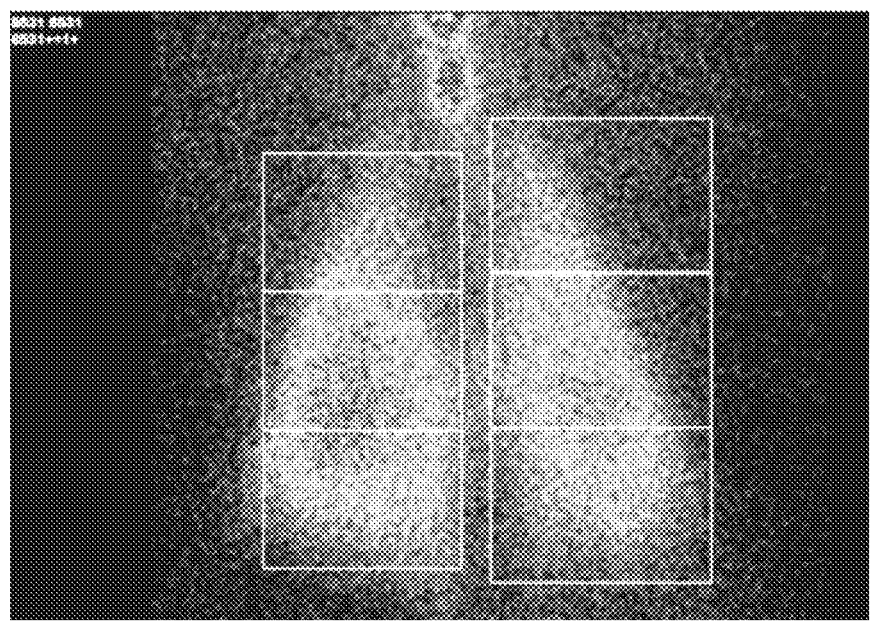

Reference is now made to FIGS. 16A-16B, which schematically represent deposition of radiolabeled diethylenetriaminepentaacetic acid (DPTA) particles, in the pig lung of FIGS. 15A-15D, according to some embodiments of the present disclosure.

FIG. 16A represents the pre-protocol state of FIGS. 15A-15B, viewed along a ventral-dorsal axis. The right lung (appearing on the left side) displays a clear deficit in deposition of DPTA particles; consistent with the lung blockage shown in FIGS. 15A-15B.

FIG. 16B represents the post-protocol state of FIGS. 15C-15D, also viewed along the ventral-dorsal axis. The pattern of particle deposition in the left and right lungs is now equalized.

General

It is expected that during the life of a patent maturing from this application many relevant pulmonary medicines will be developed; the scope of the terms medicine and drug is intended to include all such new technologies a priori.

As used herein with reference to quantity or value, the term "about" means "within ±25% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the present disclosure may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments may be presented with reference to a range format. It should be understood that the description in range format is merely for convenience and brevity and should not be construed as an inflexible limitation on the scope of descriptions of the present disclosure. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

Although descriptions of the present disclosure are provided in conjunction with specific embodiments, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

It is appreciated that certain features which are, for clarity, described in the present disclosure in the context of separate embodiments, may also be provided in combination in a single embodiment. Conversely, various features, which are, for brevity, described in the context of a single embodiment, may also be provided separately or in any suitable subcombination or as suitable in any other described embodiment of the present disclosure. Certain features described in the context of various embodiments are not to be considered essential features of those embodiments, unless the embodiment is inoperative without those elements.

What is claimed is:

1. A method of using pressure to recruit lung regions of a patient, the method comprising administering, during each of one or more breath cycles:
    during an inspiratory phase, providing a period of positive inspiration pressure extended to pressurize de-recruited lung regions via collateral airways;
    during an expiratory phase, providing a reduction from the positive inspiration pressure down to a non-negative undershoot pressure, allowing pressure in pressurized de-recruited lung regions to mobilize mucous along main branch airways of the lung; and
    providing an elevation of pressure from the undershoot pressure to a positive expiratory pressure, before lung volume reaches a breath cycle minimum; wherein:
    within a first one or more administrations during said one or more breath cycles, the positive expiratory pressure is followed by initiation of a next inspiratory phase without suction; and
    within a second one or more administrations during said one or more breath cycles following the first one or more administrations, the positive expiratory pressure is followed by a period of suction before the next inspiratory phase.

2. The method according to claim 1, wherein, after a decrease in pressure and during the expiratory phase, gradually increasing positive expiratory pressure through a range of pressures comprising a lower pressure, an upper pressure and the positive expiratory pressure.

3. The method according to claim 1, comprising, after the reduction from the positive inspiration pressure and during the expiratory phase, before lungs of the patient reach a minimum volume during the expiratory phase, increasing pressure to a positive expiratory pressure within a range between about 5 cm $H_2O$ and 9 cm $H_2O$.

4. The method according to claim 1, wherein providing pressure is performed by a device selected from a group consisting of:

a respiratory ventilator;
a cough simulation device;
a cough assistance system; and
a mechanical insufflation-exsufflation device.

5. The method according to claim 1, wherein during the inspiratory phase, positive inspiration pressure is maintained within a range of about 30-50 cm $H_2O$ of pressure for a high positive pressure period between about 0.8 seconds and 5 seconds, after an inspirium rump period.

6. The method according to claim 1, wherein during the inspiratory phase, maintaining pressure within a range of about 8-40 cm $H_2O$ of pressure for a hold period between about 1-3 seconds.

7. The method according to claim 1, wherein at onset of the expiratory phase comprising decreasing pressure to a minimum pressure below 5 cm $H_2O$.

8. The method according to claim 1, comprising:
decreasing pressure within said second one or more administrations to a first range of expiratory pressures for a period including at least 1.5 seconds at a positive expiratory pressure at onset of the expiratory phase; and
followed by, during a suction period within said second one or more administrations, decreasing pressure to a suction pressure within a range between about −20 cm $H_2O$ and about −40 cm $H_2O$.

9. The method according to claim 1, wherein the positive expiratory pressure is maintained for 2-3.5 seconds after the onset of the expiratory phase until the next inspiratory phase begins.

10. The method according to claim 1, wherein the undershoot pressure is above about 0 cm $H_2O$.

11. The method according to claim 1, wherein the positive expiratory pressure within said second one or more administrations is maintained for 0.5-2.5 seconds, and is followed by suction to a pressure within a range of −20 to −40 cm $H_2O$ before the next inspiratory phase begins.

12. The method according to claim 1 wherein:
within the first one or more administrations during said one or more breath cycles, the positive expiratory pressure is maintained for 2-3.5 seconds after the onset of the expiratory phase until the next inspiratory phase begins; and
within the second one or more administrations during said one or more breath cycles following the first one or more administrations, the positive expiratory pressure is maintained for 0.5-2.5 seconds after the onset of the expiratory phase, and is followed by suction to a pressure within a range of −20 to −40 cm $H_2O$ before the next inspiratory phase begins.

13. The method according to claim 1, comprising beginning or interrupting the administering based on monitoring pulmonary pressure using a sensor, and based on detecting a spontaneous change in sensed pulmonary pressure.

14. The method according to claim 1, comprising, during a sequence of breaths, and following said one or more breath cycles comprising administrations, administering over another one or more breath cycles a medication mode of pulmonary therapy applying medicine to the lungs, comprising an inhalation phase and an expiratory phase; and
wherein, during the inhalation phase of the medication mode of pulmonary therapy, maintaining pressure within a range of about 8-40 cm $H_2O$ of pressure for a period between about 1-3 seconds, during which said inspiratory phase medicine is released to the lungs.

15. The method according to claim 14, wherein, at onset of an expiratory phase of the medication mode of pulmonary therapy, decreasing pressure to a positive expiratory pressure lower than pressure at the inhalation phase, and within a range between about 1 cm $H_2O$ and 8 cm $H_2O$.

16. The method according to claim 14, wherein, the medicine is released to the lungs 1-3 seconds after initiation of the inhalation phase.

17. A system for collecting pulmonary data from patients and providing pulmonary physical treatment, the system comprising:
a pulmonary sensor;
a computing unit arranged to receive data measured by the pulmonary sensor and analyze the data, producing an analysis; and
a pulmonary physical treatment unit for providing pulmonary physical treatment under control by the computing unit,
wherein the computing unit is arranged to:
control the pulmonary physical treatment unit to provide pulmonary physical treatment based on the data, administering, during each of one or more breath cycles, treatment as follows:
during an inspiratory phase, a period of positive inspiration pressure extended to pressurize de-recruited lung regions via collateral airways;
during an expiratory phase, a reduction from the positive inspiration pressure down to a non-negative undershoot pressure, allowing pressure in pressurized de-recruited lung regions to mobilize mucous along main branch airways of the lung; and
elevation of pressure from the undershoot pressure to a positive expiratory pressure, before lung volume reaches a breath cycle minimum; wherein
within a first one or more administrations during said one or more breath cycles, the positive expiratory pressure is followed by initiation of a next inspiratory phase without suction, and
within a second one or more administrations during said one or more breath cycles following the first one or more administrations, the positive expiratory pressure is followed by a period of suction before the next inspiratory phase.

18. A system according to claim 17, comprising an electronically controllable valve in a hand-held unit, configured to be controllable for providing PEP (Positive Expiratory Pressure) maneuvers to the patient via a mouthpiece.

19. A system according to claim 17, comprising a pulmonary medicine unit configured for dispensing pulmonary medicine under control of the computing unit, wherein the computing unit is arranged to determine whether to control the pulmonary medicine unit to provide pulmonary medicine based on the analysis.

20. A method according to claim 1, wherein the undershoot pressure is high enough to avoid collapse of said pressurized de-recruited lung regions and causes pressure in said de-recruited lung regions to mobilize mucous along main branch airways of the lung.

21. A method according to claim 1, further comprising:
identifying a patient with de-recruited lung regions and unsatisfactory mucus clearing;
administering, during each of said one or more breath cycles said period of positive inspiration pressure followed by said reduction from the positive inspiration pressure down to said non-negative undershoot pressure and followed by said elevation of pressure from the undershoot pressure.

22. A method according to claim 1, wherein said elevation of pressure continues gradually for between 1.5 and 3.5 seconds before the lung volume reaches a minimum.

* * * * *